United States Patent
Kluckner et al.

(10) Patent No.: US 11,022,620 B2
(45) Date of Patent: Jun. 1, 2021

(54) METHODS, APPARATUS, AND QUALITY CHECK MODULES FOR DETECTING HEMOLYSIS, ICTERUS, LIPEMIA, OR NORMALITY OF A SPECIMEN

(71) Applicant: Siemens Healthcare Diagnostics Inc., Tarrytown, NY (US)

(72) Inventors: Stefan Kluckner, Berlin (DE); Shanhui Sun, Princton, NJ (US); Yao-Jen Chang, Princeton, NJ (US); Terrence Chen, Princeton, NJ (US); Benjamin S. Pollack, Jersey City, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 197 days.

(21) Appl. No.: 16/349,075

(22) PCT Filed: Nov. 13, 2017

(86) PCT No.: PCT/US2017/061396
§ 371 (c)(1),
(2) Date: May 10, 2019

(87) PCT Pub. No.: WO2018/089938
PCT Pub. Date: May 17, 2018

(65) Prior Publication Data
US 2019/0277870 A1    Sep. 12, 2019

Related U.S. Application Data

(60) Provisional application No. 62/421,957, filed on Nov. 14, 2016.

(51) Int. Cl.
*G01N 35/00* (2006.01)
*G06T 7/11* (2017.01)
(Continued)

(52) U.S. Cl.
CPC ........ *G01N 35/00732* (2013.01); *B01L 9/523* (2013.01); *G01J 3/10* (2013.01);
(Continued)

(58) Field of Classification Search
None
See application file for complete search history.

(56) References Cited

U.S. PATENT DOCUMENTS 8,310,658 B2    11/2012  Wardlaw et al.
9,322,761 B2 *   4/2016  Miller .................... G01N 15/05
(Continued)

FOREIGN PATENT DOCUMENTS

CN    1809739 A    7/2006
CN   107624193 A   1/2018
(Continued)

OTHER PUBLICATIONS

PCT International Search Report and Written Opinion dated Mar. 13, 2018 (16 Pages).
(Continued)

*Primary Examiner* — Anand P Bhatnagar

(57) ABSTRACT

A method of characterizing a specimen for HILN (H, I, and/or L, or N). The method includes capturing images of the specimen at multiple different viewpoints, processing the images to provide segmentation information for each viewpoint, generating a semantic map from the segmentation information, selecting a synthetic viewpoint, identifying front view semantic data and back view semantic data for the synthetic viewpoint, and determining HILN of the serum or plasma portion based on the front view semantic data with an HILN classifier, while taking into account back view semantic data. Testing apparatus and quality check modules adapted to carry out the method are described, as are other aspects.

20 Claims, 7 Drawing Sheets

(51) Int. Cl.
*B01L 9/00* (2006.01)
*G01N 21/27* (2006.01)
*G06T 7/00* (2017.01)
*G01J 3/10* (2006.01)
*G01N 21/25* (2006.01)
*G01J 3/28* (2006.01)
*G06T 5/50* (2006.01)
*G01B 11/00* (2006.01)
*G01B 11/06* (2006.01)

(52) U.S. Cl.
CPC ............ *G01J 3/108* (2013.01); *G01J 3/2823* (2013.01); *G01N 21/25* (2013.01); *G01N 21/27* (2013.01); *G01N 35/00* (2013.01); *G01N 35/00584* (2013.01); *G01N 35/00603* (2013.01); *G06T 5/50* (2013.01); *G06T 7/0012* (2013.01); *G06T 7/11* (2017.01); *B01L 2200/18* (2013.01); *B01L 2300/021* (2013.01); *B01L 2300/0609* (2013.01); *G01B 11/00* (2013.01); *G01B 11/06* (2013.01); *G01J 2003/104* (2013.01); *G01J 2003/106* (2013.01); *G06T 2207/10144* (2013.01); *G06T 2207/10152* (2013.01); *G06T 2207/20221* (2013.01); *G06T 2207/30024* (2013.01)

(56) References Cited

U.S. PATENT DOCUMENTS

| | | | |
|---|---|---|---|
| 10,209,267 B1 * | 2/2019 | Kowalchuk | G01N 35/00871 |
| 10,267,813 B1 * | 4/2019 | Bhatia | G01N 15/05 |
| 10,429,401 B2 * | 10/2019 | Streibl | G01N 35/1016 |
| 10,527,635 B1 * | 1/2020 | Bhatia | G01N 35/00603 |
| 10,705,103 B2 * | 7/2020 | Pollack | G01N 35/026 |
| 10,746,753 B2 * | 8/2020 | Kluckner | G01N 35/1016 |
| 10,816,538 B2 * | 10/2020 | Kluckner | G01N 33/492 |
| 2005/0163354 A1 | 7/2005 | Ziegler | |
| 2012/0140230 A1 * | 6/2012 | Miller | G01N 15/05 356/441 |
| 2013/0076882 A1 | 3/2013 | Itoh | |
| 2015/0241457 A1 | 8/2015 | Miller | |
| 2017/0178321 A1 * | 6/2017 | Nieves Alicea | G06K 9/6267 |
| 2018/0045654 A1 | 2/2018 | Park et al. | |
| 2018/0364268 A1 | 12/2018 | Kluckner et al. | |
| 2018/0365530 A1 | 12/2018 | Kluckner et al. | |
| 2018/0372648 A1 * | 12/2018 | Wissmann | G06K 9/6212 |
| 2018/0372715 A1 | 12/2018 | Kluckner et al. | |
| 2019/0033230 A1 | 1/2019 | Kluckner et al. | |
| 2019/0271714 A1 * | 9/2019 | Kluckner | G01N 21/25 |
| 2020/0098105 A1 * | 3/2020 | Nieves Alicea | G06K 9/4661 |

FOREIGN PATENT DOCUMENTS

| | | |
|---|---|---|
| JP | 2005-098832 A | 4/2005 |
| JP | 2013-501937 A | 1/2013 |
| JP | 2015-014506 A | 1/2015 |
| WO | 2016/133900 A1 | 8/2016 |
| WO | 2016/175773 A1 | 11/2016 |

OTHER PUBLICATIONS

Murase, Kenya: "Utilization of Medical Images in Clinical Setting", Journal of the Imaging Society of Japan, vol. 45, No. 4, pp. 32-37.
Pu, Ningjing et al: "Performance evaluation of CS5100 automatic blood coagulation analyzer"; Chinese Journal of Thrombosis and Ilemostasis 2016; vol. 22; No. 2; Dec. 31, 2016; CN pp. 178-185.

* cited by examiner

METHODS, APPARATUS, AND QUALITY CHECK MODULES FOR DETECTING HEMOLYSIS, ICTERUS, LIPEMIA, OR NORMALITY OF A SPECIMEN

CROSS-REFERENCE TO RELATED APPLICATIONS

This application claims priority to U.S. provisional application Ser. No. 62/421,957 filed on Nov. 14, 2016, the contents of which is incorporated herein by reference in its entirety.

FIELD

The present disclosure relates to methods and apparatus for testing of a specimen, and, more particularly to methods and apparatus for determining if a specimen includes hemolysis (H), icterus (I), and/or lipemia (L), or is normal (N).

BACKGROUND

Automated testing systems may be used to conduct clinical chemistry or assay testing using one or more reagents to identify an analyte or other constituent in a specimen such as urine, blood serum, blood plasma, interstitial liquid, cerebrospinal liquids, or the like. For convenience and safety reasons, these specimens may be contained within specimen containers (e.g., blood collection tubes). The assay or test reactions generate various changes that may be read and/or manipulated to determine a concentration of analyte or other constituent present in the specimen.

Improvements in automated testing technology have been accompanied by corresponding advances in pre-analytical specimen preparation and handling operations such as sorting, batch preparation, centrifuging of specimen containers to separate specimen constituents, cap removal to facilitate specimen access, and the like by automated, pre-analytical, specimen preparation systems, which may be part of a Laboratory Automation System (LAS). The LAS may automatically transport specimens in specimen containers to one or more pre-analytical specimen processing stations as well as to analyzer stations containing clinical chemistry analyzers and/or assay instruments (hereinafter collectively "analyzers").

These LASs may handle processing of a number of different specimens at one time, which may be contained in barcode-labeled (hereinafter including a "label") specimen containers. The label may contain an accession number that may be correlated to demographic information that may be entered into a hospital's Laboratory Information System (LIS) along with test orders and/or other information. An operator may place the labeled specimen containers onto the LAS system, which may automatically route the specimen containers for one or more pre-analytical operations such as centrifugation, decapping, and aliquot preparation, and all prior to the specimen actually being subjected to clinical analysis or assaying by one or more analyzers that may be part of the LAS.

For certain tests, such as for detection of an interferent, such as H, I, and/or L, a serum or plasma portion obtained from whole blood by fractionation (e.g., by centrifugation) may be subjected to testing. A gel separator may be added to the specimen container to aid in the separation of the settled blood portion from the serum or plasma portion in some embodiments. After fractionation and a subsequent de-capping process, in some embodiments the specimen container may be transported to an appropriate analyzer that may extract, via aspiration, serum or plasma portion from the specimen container and combine the serum or plasma portion with one or more reagents in a reaction vessel (e.g., cuvette or other vessel). Analytical measurements may then be performed, often using a beam of interrogating radiation, for example, or by using photometric or fluorometric absorption readings, or the like. The measurements allow determination of end-point or rate values, from which a concentration of analyte or other constituent may be determined using well-known techniques.

Unfortunately, the presence of any interferent (e.g., H, I, and/or L) in the specimen, as a result of a patient condition or sample processing, may possibly adversely affect the test results of the analyte or constituent measurement obtained from the analyzer. For example, the presence of hemolysis in the specimen, which may be unrelated to the patient disease state, may cause a different interpretation of the disease condition of the patient. Moreover, the presence of icterus and/or lipemia in the specimen may also cause a different interpretation of the disease condition of the patient.

In the prior art, the integrity of the serum or plasma portion of the specimen may be visually inspected and rated for a degree of H, I, and/or L (e.g., by assigning an index) by a skilled laboratory technician. This may involve a review of the color of the serum or plasma portion of the specimen against known standards. A normal (N) serum or plasma portion has a light yellow to light amber color. Serum or plasma portion containing hemolysis may have a reddish color. Serum or plasma portion containing icterus may have a dark yellow color due to increased bilirubin, and serum or plasma portion containing lipemia may have a whitish or milky appearance. Depending on the color, the laboratory technician assigns an index. However, such visual inspection is very subjective, labor intensive, and fraught with the possibility of human error.

Because manual inspection includes the problems listed above, it is sought to evaluate the integrity of the specimen without the use of visual inspection by a laboratory technician, but rather by using an automated inspection method. However, in some instances, one or more labels adhered directly to the specimen container may partially occlude the view of the specimen, so that there may not be clear opportunity to visually observe the serum or plasma portion. Thus, automation of such pre-analysis processes is difficult.

To accommodate for this, some systems, such as those described in U.S. Pat. No. 9,322,761 to Miller entitled "Methods And Apparatus For Ascertaining Interferents And Physical Dimensions in Liquid Samples And Containers To Be Analyzed By A Clinical Analyzer" describes automated pre-screening for HILN by rotating the specimen container to find a view window that is unobstructed by the label and then carrying out imaging. However, such systems may be less prone to ease of automation.

Because of problems encountered when a condition of hemolysis, icterus, or lipemia (HIL) is contained within a specimen to be analyzed, there is an unmet need for a method and apparatus adapted to readily determine a presence of HIL and possibly the extent thereof. The method and apparatus should not appreciably adversely affect the speed at which analytical or assaying test results are obtained, i.e., the time to determine the presence of H, I, and/or L or N should be very short. Furthermore, the method and apparatus should be able to be used even on labeled specimen containers where the label occludes some portion of the serum or plasma portion of the specimen.

SUMMARY

According to a first aspect, a method of characterizing a specimen for HILN is provided. The method includes capturing one or more images from multiple viewpoints of a specimen container including a serum or plasma portion, wherein the specimen container is held in a holder and some portion of the specimen container includes a label, processing the one or more images from the multiple viewpoints to provide segmentation information for each of the multiple viewpoints by determining classifications of regions for each of the multiple viewpoints, generating a semantic map from the segmentation information from each of the multiple viewpoints, selecting a synthetic viewpoint that has visibility of the serum or plasma portion, identifying front view semantic data and back view semantic data for the synthetic viewpoint, and determining HILN of the serum or plasma portion based on the front view semantic data with an HILN classifier, while taking into account the back view semantic data.

According to another aspect, a quality check module adapted to determine presence of an interferent in a specimen contained within a specimen container is provided. The quality check module includes a plurality of image capture devices arranged around the specimen container and configured to capture multiple images of the specimen from multiple viewpoints; and a computer coupled to the plurality of image capture devices and adapted to process image data of the multiple images, the computer configured and capable of being operated to: generate a semantic map, select a synthetic viewpoint of the semantic map, identify front view semantic data and back view semantic data for the synthetic viewpoint, and classify whether an interferent is present within a serum or plasma portion of the specimen based on the front view semantic data, while taking into account the back view semantic data.

In another aspect, a specimen testing apparatus adapted to determine presence of an interferent in a specimen contained within a specimen container is provided. The specimen testing apparatus includes a track; a carrier moveable on the track and configured to contain the specimen container; a plurality of image capture devices arranged around the track and configured to capture multiple images of the specimen from multiple viewpoints; and a computer coupled to the plurality of image capture devices and configured to process image data from the multiple images, the computer configured and capable of being operated to: generate a semantic map, select a synthetic viewpoint of the semantic map, identify front view semantic data and back view semantic data for the synthetic viewpoint, and classify whether an interferent is present within a serum or plasma portion of the specimen based on the front view semantic data, while taking into account the back view semantic data.

Still other aspects, features, and advantages of the present disclosure may be readily apparent from the following description by illustrating a number of example embodiments and implementations, including the best mode contemplated for carrying out the present invention. The present invention may also be capable of other and different embodiments, and its several details may be modified in various respects, all without departing from the scope of the present invention. The disclosure is intended to cover all modifications, equivalents, and alternatives falling within the scope of the appended claims.

BRIEF DESCRIPTION OF THE DRAWINGS

The drawings, described below, are for illustrative purposes and are not necessarily drawn to scale. Accordingly, the drawings and descriptions are to be regarded as illustrative in nature, and not as restrictive. The drawings are not intended to limit the scope of the invention in any way.

DETAILED DESCRIPTION

Figure 1:
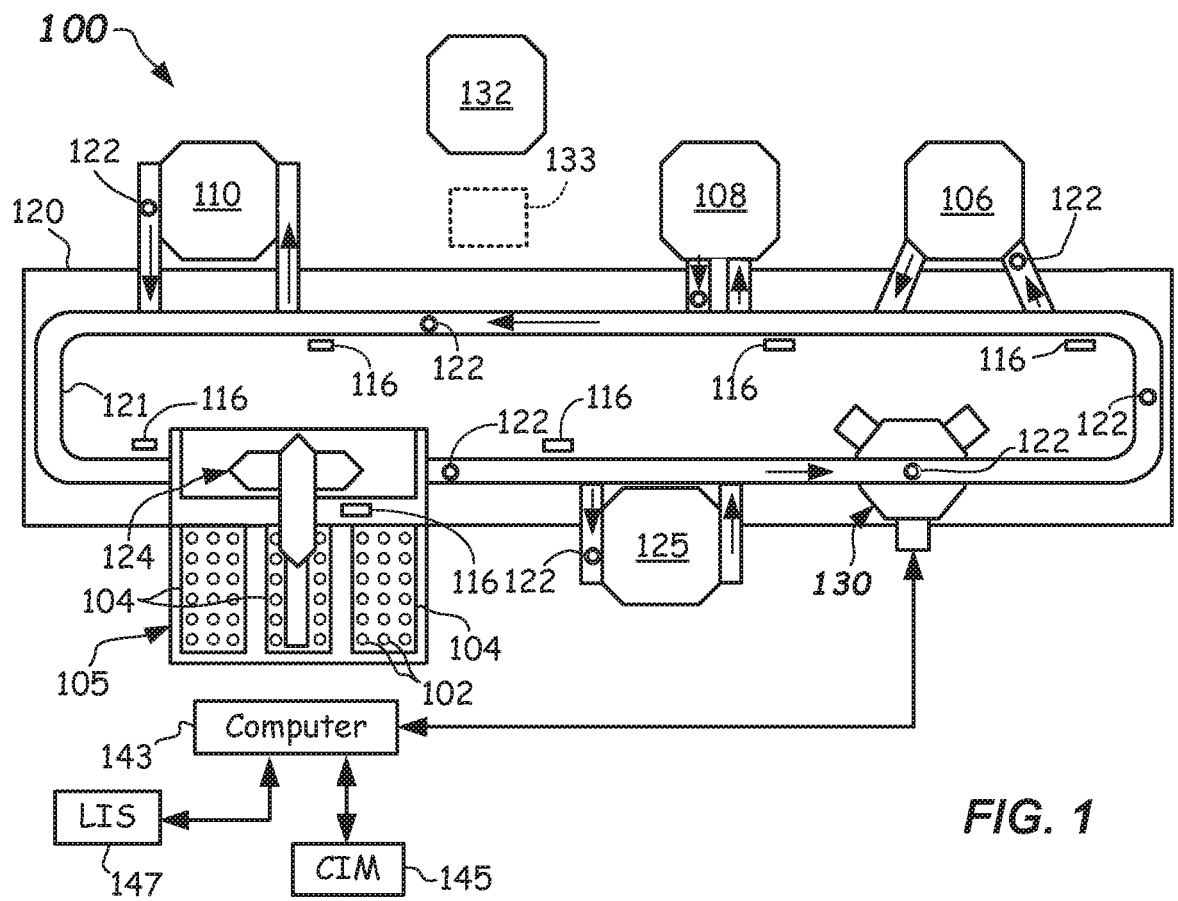
FIG. 1 illustrates a top schematic view of a specimen testing apparatus including one or more quality check modules configured to detect H, I, and/or L or N of a specimen and one or more analyzers (clinical chemistry or assay instruments) according to one or more embodiments.

In a first broad aspect, embodiments of the present disclosure provide methods and apparatus configured to determine if an interferent is present in a serum or plasma portion of a specimen, or whether the serum or portion is normal (N), i.e., does not contain an interferent. "Interferent," as used herein, means the presence of at least one of hemolysis (H), icterus (I), or lipemia (L) in the serum or plasma portion of the specimen. Hemolysis (H), icterus (I), and lipemia (L) are collectively referred to as "HIL" herein.

"Hemolysis" as used herein is defined as a condition in the serum or plasma portion wherein during processing red blood cells are destroyed, which leads to the release of hemoglobin from the red blood cells into the serum or plasma portion such that the serum or plasma portion takes on a reddish hue. The degree of Hemolysis may be quantified by assigning a Hemolysis index.

"Icterus" as used herein means a condition of the blood where the serum or plasma portion is discolored dark yellow caused by an accumulation of bile pigment (bilirubin) in the blood. The degree of Icterus may be quantified by assigning an Icteric index.

"Lipemia" as used herein means a presence in the blood of an abnormally high concentration of emulsified fat, such that the serum or plasma portion includes a whitish or milky appearance. The degree of lipemia may be quantified by assigning a Lipemic index.

The presence of one or more interferent (HIL) in the serum or plasma portion, as discussed above, may affect the interpretation of results of the subsequent testing by the one or more analyzers (e.g. clinical chemistry or assay testing). Thus, the ability to pre-screen for HIL before final analysis by an analyzer may advantageously minimize wasted time analyzing specimens that are not of the proper quality for analysis. Specimens that are found to contain or more of HIL may be flagged to the operator, scheduled for a redraw, subjected to a remediation process, or subjected to further testing to more accurately measure an extent of the interferent that is present.

The specimen, as described herein, is collected in a specimen container, such as a blood collection tube and includes a settled blood portion and a serum and plasma portion after fractionation (e.g., separation by centrifugation). The settled blood portion is made up blood cells such as white blood cells (leukocytes), red blood cells (erythrocytes), and platelets (thrombocytes), which are aggregated and separated from the serum or plasma portion. The settled blood portion is found at a bottom part of the specimen container.

The serum or plasma portion is the liquid component of blood, which is not part of the settled blood portion. It is found above the settled blood portion after fractionation. Plasma and serum differ in the content of coagulating components, primarily fibrinogen. Plasma is the unclotted liquid, whereas serum refers to blood plasma, which has been allowed to clot either under the influence of endogenous enzymes or exogenous components. In some specimen containers, a small gel separator may be used, which positions itself between the settled blood portion and the serum or plasma portion during centrifugation. The gel separator serves as a physical barrier between the two portions (liquid and solid).

In accordance with one or more embodiments, the interferent detection method may be carried out as a pre-analytical testing method, i.e., taking place before carrying out analysis on an analyzer (e.g., clinical chemistry or assaying instrument). The H, I, and/or L or N detection method described herein may, in some embodiment, use high dynamic range (HDR) image processing of the serum or plasma portion of the specimen to determine the presence of an interferent (H, I, and/or L or N). In some embodiments, the identification of the physical boundaries of the serum or plasma portion may also take place during a segmentation process by using HDR image processing.

In one or more embodiments, a quality check module may be configured to carry out the interferent detection method. The quality check module may be provided in an area where a robotic mechanism (e.g., a track or gripper-finger robot) may facilitate transport of specimens contained in specimen containers to the quality check module. In some embodiments, the quality check module may be provided on the track, where the track carries the specimens to remote locations for analysis (e.g., clinical chemistry testing or assaying) on an analyzer. In some embodiments, the quality check module may be provided on the track so that the specimen may be tested for the presence of an interferent while being resident on the track. In these instances, the specimen container may be held in an upright position by a specimen container holder (hereinafter "holder"). The holder may include fingers that hold the specimen container, and these fingers may be oriented such that some or all of the fingers are located within the image window the image capture device, as will be apparent from the following.

In one or more embodiments, the processed data (e.g., HDR data) may be used for the HILN detection. In further embodiments, the data may also be used for artifact detection (e.g., the detection of clot, bubble, or foam in the serum or plasma portion). In this case, the pixels that are found to contain an artifact may simply be ignored in carrying out the determination of HILN based upon the processed data, as the artifact location(s) and its extent is known.

Should the specimen be found to contain one or more of H, I, and L, the specimen may then be taken off line to perform a remediation to rectify the one or more of H, I, or L, for further quantification of the extent of the H, I, or L, for a redraw, or for other processing. The interferent detection method described herein is image based, i.e., based on pixelated images obtained by multiple image capture devices located so as to capture images at multiple viewpoints. "Pixelated image" as used herein means images including either single pixels or a grouping of pixels, such as a super-pixels or image patches including more than one pixel. A super pixel or image patch having a size of 11 individual pixels by 11 individual pixels was found to work well for efficient processing of the data.

The HILN detection method described herein may include capturing multiple images at the quality check module. The images may be captured at multiple exposure times and at multiple spectra having different nominal wavelengths and from the multiple viewpoints using a plurality of image capture devices. "Image capture devices" as used herein means any device capable of capturing a pixelated image (e.g., digital image) for analysis, such as a digital camera, a CCD (charge-coupled device) and CMOS (complementary metal-oxide semiconductor), an array of sensors, or the like. The exposure time may vary based on the lighting intensity and features of the image capture devices, but multiple exposure times may be used for each spectrum and for each image capture device. For each image capture devices, the exposure time may be the same for each corresponding image capture.

For each corresponding pixel of the multiple captured images at a particular spectrum, pixels exhibiting optimal image intensity may be selected. The result may be a plurality of consolidated color image data sets for each different spectrum (e.g., red, green, blue, or the like) where all of the pixels are optimally exposed (e.g., one image data set per spectrum (e.g., red, green, blue, or the like)). The data from the consolidated color data sets may be subject to statistical analysis to determine statistical data on each pixel (e.g., mean, standard deviation, and covariance matrix)

thereof. Covariance is a measure of how much two or more of the color pixels change together. This statistical data, in the form of one or more data matrices, can then be operated on by or more multi-class classifiers in order to segment the image data set into classes (hereinafter "segmentation").

The segmentation may determine the area of the serum or plasma portion in the image, as well as other classes (e.g., settled blood portion, gel separator, tube, cap, label, holder, air). The multi-class classifier may be a support vector machine (SVM) or a random decision tree that has been pre-trained from multiple training sets. Once the serum or plasma portion is identified by the multi-class classifier, one or more interferent classifiers may be used to directly identify and classify the presence of an interferent (e.g., H, I, and/or L) or normality (N). The one or more interferent classifiers may be individually trained binary models that may classify each pixel (or superpixel/image patch) as being H, I, or L, or N, respectively. In other embodiments, the interferent classifier may be a multi-class classifier. The interferent classifier models may each also be a support vector machine (SVM) or a random decision tree.

Although using the images from multiple viewpoints can provide acceptable results in terms of properly characterizing HILN, it has been discovered by the inventors herein that the presence of the label and/or holder on the back side of the specimen container from the viewpoint where the image is captured can affect the image captured at that viewpoint. For example, if the label or portions of the holder are located on the backside of the specimen container from one viewpoint, the presence thereof may obscure the back light that can pass through the serum or plasma portion and thus affect the image intensity capable of being measured by the image capture device at that viewpoint. Embodiments of the present disclosure may account for the presence of such label and/or holder on the backside. This compensation may be accomplished by generating a semantic model, which takes into account the backside information. From this a semantic model, a more accurate determination of HILN may be provided.

Moreover, based upon the more accurate interferent classification results, an interferent type for the serum or plasma portion, as a whole, may be determined (i.e., H, I, and/or L or N) from the semantic model. An interferent level for the determined interferent type(s) may also be optionally provided. The interferent level may be based upon one or more additional models (e.g., one or more regression models) in some embodiments. The regression models may be trained for each interferent type based upon sample specimens that exhibit diverse interference levels. More than one interferent type may be determined by the method, and an interferent level for each determined interferent type may be specified.

Further details of inventive interferent detection methods, quality check modules configured to carry out the method, and specimen testing apparatus including one or more quality check modules will be further described with reference to FIGS. 1-7 herein.

Figure 2A:
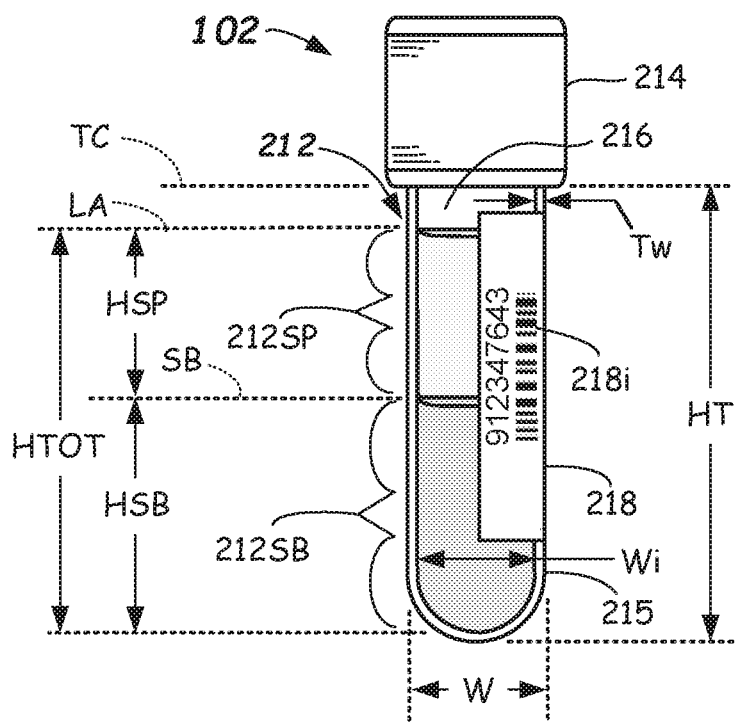
FIG. 2A illustrates a side view of a specimen container including a separated specimen with a serum or plasma portion containing an interferent, and wherein the specimen container includes a label thereon.
Figures 2B, 3:
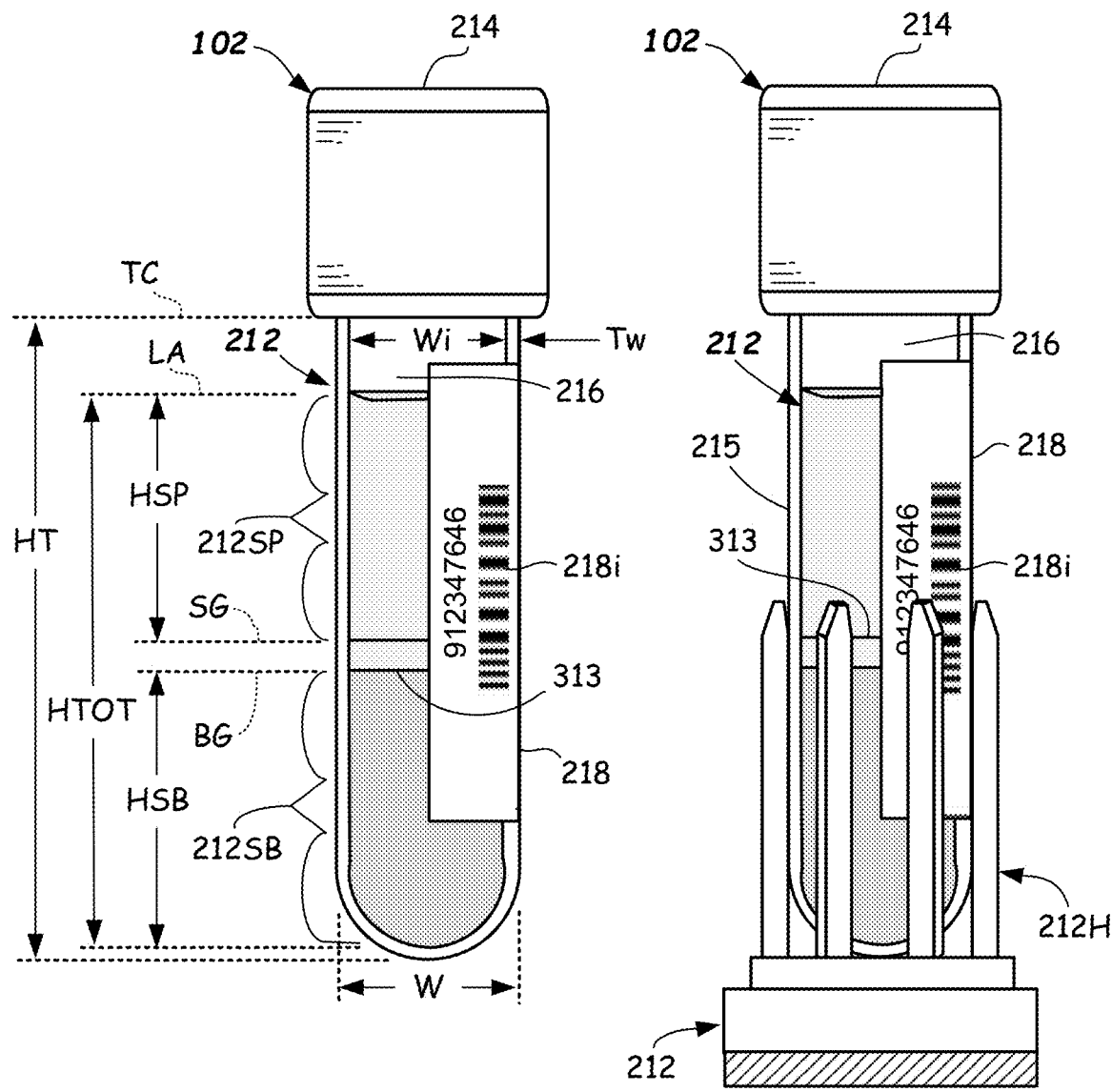
FIG. 2B illustrates a side view of a specimen container including a label, a separated specimen including a serum or plasma portion containing an interferent, and a gel separator.
FIG. 3 illustrates a side view of a specimen container including a label, a separated specimen containing an interferent in the serum or plasma portion, a gel separator, and wherein the specimen container is shown being held in an upright orientation in a holder.

FIG. 1 shows a specimen testing apparatus 100 capable of automatically processing multiple specimen containers 102 (e.g., see FIGS. 2A-3). The specimen containers 102 may be contained in one or more racks 104 at a loading area 105 prior to transportation to and analysis by one or more analyzers (e.g., first, second, and third analyzer 106, 108, 110, respectively, arranged about the specimen testing apparatus 100). It should be apparent that more or less numbers of analyzers can be used. The analyzers may be any combination of clinical chemistry analyzers and/or assaying instruments, or the like. The specimen containers 102 may be any transparent or translucent container, such as a blood collection tube, test tube, sample cup, cuvette, or other clear or opaque glass or plastic container capable of containing the specimen 212.

Typically, specimens 212 (FIGS. 2A-3) to be automatically processed may be provided to the specimen testing apparatus 100 in the specimen containers 102, which may be capped with a cap 214. The caps 214 may have different shapes and/or colors (e.g., red, royal blue, light blue, green, grey, tan, yellow, or color combinations) which may have meaning in terms of the test the specimen container 102 is used for, the type of additive, or the like. Other colors may be used.

Each of the specimen containers 102 may be provided with a label 218 including identification information 218$i$ (i.e., indicia), such as a barcode, alphabetic, numeric, alphanumeric, or combination thereof that may be machine readable at various locations about the specimen testing apparatus 100. The identification information 218$i$ may indicate, or may otherwise be correlated to, via a Laboratory Information System (LIS) 147, a patient's identification as well as tests to be accomplished upon the specimen 212, or other information, for example. Such identification information 218$i$ may be provided on a label 218 adhered to the tube 215. The label 218 may not extend all the way around the specimen container 102, or all along a length of the specimen container 102. In some embodiments multiple labels 218 may be adhered, and may slightly overlap. Accordingly, although the label(s) 218 may occlude some portion of the specimen 212, some portion of the specimen 212 may still be viewable from at least one viewpoint. In some embodiments, the racks 104 may have additional identification information thereon.

The specimen 212 may include a serum or plasma portion 212SP and a settled blood portion 212SB contained within the tube 215. Air 216 may be provided above the serum and plasma portion 212SP and the line or demarcation between them is defined herein as the liquid-air interface (LA). The line of demarcation between the serum or plasma portion 212SP and the settled blood portion 212SB is defined herein as the serum-blood interface (SB). The interface between the air 216 and the cap 214 is referred to herein as the tube-cap interface (TC). The height of the tube (HT) is defined as the height from the bottom-most part of the tube 215 to the bottom of the cap 214. The height of the serum or plasma portion 212SP is (HSP) and is defined as the height from the top of the serum or plasma portion 212SP from the top of the settled blood portion 212SB, i.e., from LA to SB. The height of the settled blood portion 212SB is (HSB) and is defined as the height from the bottom of the settled blood portion 212SB to the top of the settled blood portion 212SB at SB. HTOT is the total height of the specimen 212 and equals HSP plus HSB.

In cases where a gel separator 313 is used (FIG. 2B), the height of the serum or plasma portion 212SP is (HSP) and is defined as the height from the top of the serum or plasma portion 212SP at LA to the top of the gel separator 313 at SG, i.e., from LA to SG. The height of the settled blood portion 212SB is (HSB) and is defined as the height from the bottom of the settled blood portion 212SB to the bottom of the gel separator 313 at BG. HTOT is the total height of the specimen 212 and equals HSP plus HSB plus height of the gel separator 313. In each case, the wall thickness is Tw, the outer width is W and the inner width of the specimen container 102 is Wi.

In more detail, specimen testing apparatus 100 may include a base 120 (e.g., a frame or other structure) upon which a track 121 may be mounted. The track 121 may be a railed track (e.g., a mono rail or a multiple rail), a collection of conveyor belts, conveyor chains, moveable platforms, or any other suitable type of conveyance mechanism. Track 121 may be circular or any other suitable shape and may be a closed track (e.g., endless track) in some embodiments. Track 121 may, in operation, transport individual ones of the specimen containers 102 to locations spaced about the track 121 in carriers 122.

Carriers 122 may be passive, non-motored pucks that may be configured to carry a single specimen container 102 on the track 121, or optionally, an automated carrier including an onboard drive motor, such as a linear motor that is programmed to move about the track 121 and stop at pre-programmed locations. Carriers 122 may each include a holder 122H (FIG. 3) configured to hold the specimen container 102 in a defined upright position. The holder 122H may include a plurality of fingers or leaf springs that secure the specimen container 102 to the carrier 122, but are moveable or flexible to allow for different sizes of specimen containers 102 to be received therein. In some embodiments, carriers 122 may leave from the loading area 105 having one or more racks 104 staged thereat. In some embodiments, loading area 105 may serve a dual function of allowing offloading of the specimen containers 102 from the carriers 122 after analysis is completed.

A robot 124 may be provided at the loading area 105 and may be configured to grasp the specimen containers 102 from the one or more racks 104 and load the specimen containers 102 onto the carriers 122, such as on an input lane of the track 121. Robot 124 may also be configured to remove specimen containers 102 from the carriers 122 upon completion of testing. The robot 124 including one or more (e.g., least two) robot arms or components capable of X and Z, Y and Z, X, Y, and Z, or r and theta motion. Robot 124 may be a gantry robot, an articulated robot, an R-theta robot, or other suitable robot wherein the robot 124 may be equipped with robotic gripper fingers sized and adapted to pick up and place the specimen containers 102.

Upon being loaded onto track 121, the specimen containers 102 carried by carriers 122 may progress to a first pre-processing station 125 (e.g., an automated centrifuge configured to carry out fractionation of the specimen 212). Carriers 122 carrying specimen containers 102 may be diverted to the first pre-processing station 125 by inflow lane or other suitable robot. After being centrifuged, the specimen containers 102 may exit on outflow lane, or otherwise be removed by a robot, and continue on the track 121. In the depicted embodiment, the specimen container 102 in carrier 122 may next be transported to a quality check module 130 to be further described herein with reference to FIGS. 4A and 4D.

The quality check module 130 is configured and adapted for automatically determining a presence of one or more of H, I, and/or L contained in a specimen 212 to be processed by the specimen testing apparatus 100. If found to contain effectively low amounts of H, I and/or L so as to be considered normal (N), the specimens 212 may continue on the track 121 and then may be analyzed in the one or more analyzers (e.g., first, second and third analyzers 106, 108, and/or 110) before returning each specimen container 102 to the loading area 105 for offloading. In some embodiments, the specimen 212 may also be tested for the presence of an artifact (e.g., clot, bubble, or foam) at the quality check module 130. In some embodiments, quantification of the specimen 212 may take place at the quality check module 130 (i.e., determination of HSP, HSB, HTOT, and determination of location of SB, LA). In some embodiments, characterization of the physical attributes of the specimen container 102 may take place at the quality check module 130. Such characterization may include determining HT, cap color, cap type, TC, tube width (W), and inner width (Wi).

In some embodiments, a remote station 132 may be provided on the testing apparatus 100 even though the remote station 132 is not directly linked to the track 121. For instance, an independent robot 133 (shown dotted) may carry specimen containers 102 containing specimens 212 to the remote station 132 and return them after testing/processing. Optionally, the specimen containers 102 may be manually removed and returned. Remote station 132 may be used to test for certain constituents, such as a hemolysis level, or may be used for further processing, such as to lower a lipemia level through one or more additions, or to remove a clot, bubble or foam, for example. Other testing or processing may be accomplished on remote station 132. Other stations may be provided along the track 121. Further, additional stations, not shown, may include a de-capping station, one or more additional quality check module 130, or the like.

The specimen testing apparatus 100 may include a number of sensors 116 at one or more locations around the track 121. Sensors 116 may be used to detect a location of specimen containers 102 along the track 121 by means of reading the identification information 218i placed on the specimen container 102, or like information (not shown) that is provided on each carrier 122. In some embodiments, a distinct RFID chip may be embedded in each carrier 122 and conventional RFID reader system may be employed in the tracking operation, for example. Other means for tracking the location may be used, such as proximity sensors. All of the sensors 116 may interface with the computer 143, so that the location of each specimen container 102 may be appropriately known at all times.

First pre-processing station 125 and each of the analyzers 106, 108, 110 may be equipped with robotic mechanisms and/or inflow lanes configured to remove carriers 122 from the track 121, and robotic mechanisms and/or outflow lanes configured to reenter carriers 122 to the track 121.

Specimen testing apparatus 100 may be controlled by the computer 143, which may be a microprocessor-based central processing unit CPU, having a suitable memory and suitable conditioning electronics and drivers for operating the various system components. Computer 143 may be housed as part of, or separate from, the base 120 of the specimen testing apparatus 100. The computer 143 may operate to control movement of the carriers 122 to and from the loading area 105, motion about the track 121, motion to and from the first pre-processing station 125 as well as operation of the first pre-processing station 125 (e.g., centrifuge), motion to and from the quality check module 130 as well as operation of the quality check module 130, and motion to and from each analyzer 106, 108, 110 as well as operation of each analyzer 106, 108, 110 for carrying out the various types of testing (e.g., assay or clinical chemistry).

For all but the quality check module 130, the computer 143 may control the specimen testing apparatus 100 according to software, firmware, and/or hardware commands or circuits such as those used on the Dimension® clinical chemistry analyzer sold by Siemens Healthcare Diagnostics Inc. of Tarrytown, N.Y., and such control is typical to those skilled in the art of computer-based electromechanical control programming and will not be further described herein. However, other suitable systems for controlling the specimen testing apparatus 100 may be used. The control of the quality check module 130 may also be provided by the computer 143, but according to an inventive method, as will be described in detail herein.

Embodiments of the disclosure may be implemented using a computer interface module (CIM) 145 that allows for a user to easily and quickly access a variety of control and status display screens. These control and status display screens may describe some or all aspects of a plurality of interrelated automated devices used for preparation and analysis of specimens 212. The CIM 145 may employed to provide information about the operational status of a plurality of interrelated automated devices as well as information describing the location of any specimen 212 as well as a status of tests to be performed on, or being performed on, the specimen 212. The CIM 145 is thus adapted to facilitate interactions between an operator and the specimen testing apparatus 100. The CIM 145 may include a display screen adapted to display a menu including icons, scroll bars, boxes, and buttons through which the operator may interface with the specimen testing apparatus 100. The menu may comprise a number of function buttons programmed to display functional aspects of the specimen testing apparatus 100.

In FIGS. 2A-2B and 3, specimen containers 102 including one of H, I or L are shown. FIG. 2A illustrates a specimen 212 including H, I, or L in the serum or plasma portion 212SP without a gel separator. FIG. 2B illustrates a specimen 212 including H, I, or L in the serum or plasma portion 212SP with a gel separator 313. Pre-screening the specimen containers 102 for the presence of an interferent ensures that the specimen 212 can be stopped from progressing on to the one or more analyzers 106, 108, 110. In this way, inaccurate test results may be avoided. In some embodiments, if the HILN determination method determines that an interferent exists, then the specimen container 102 may be taken offline, such as to remote station 132 for remedial action (e.g., lipemia reduction), for better quantification of the level of hemolysis or icterus, which can be reported along with the test results, or possibly to have the specimen 212 redrawn.

Figure 4A:
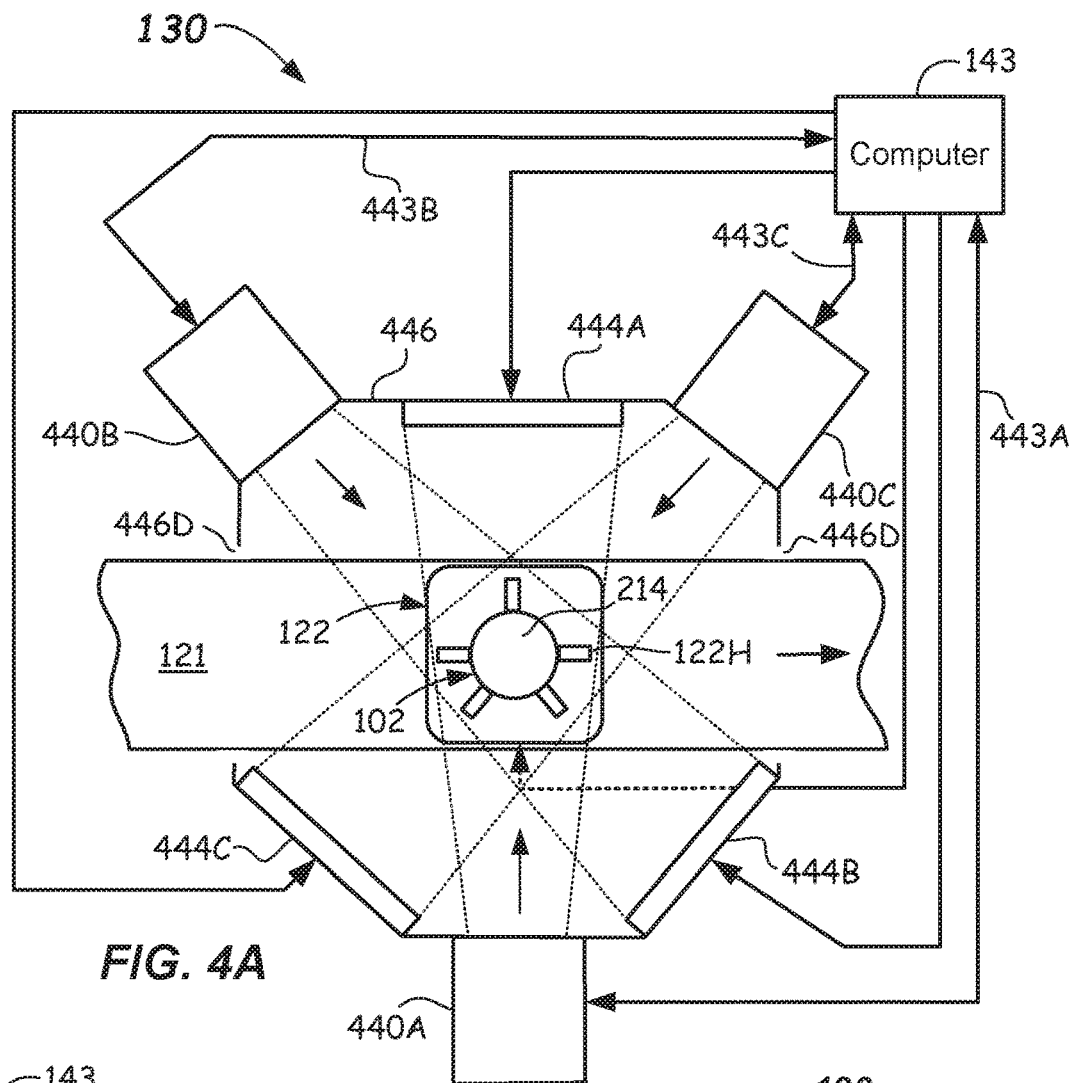
FIG. 4A illustrates a schematic top view of a quality check module (with ceiling removed) including multiple viewpoints and configured to capture and analyze multiple backlit images to enable determining a presence of an interferent according to one or more embodiments.
Figure 4B:
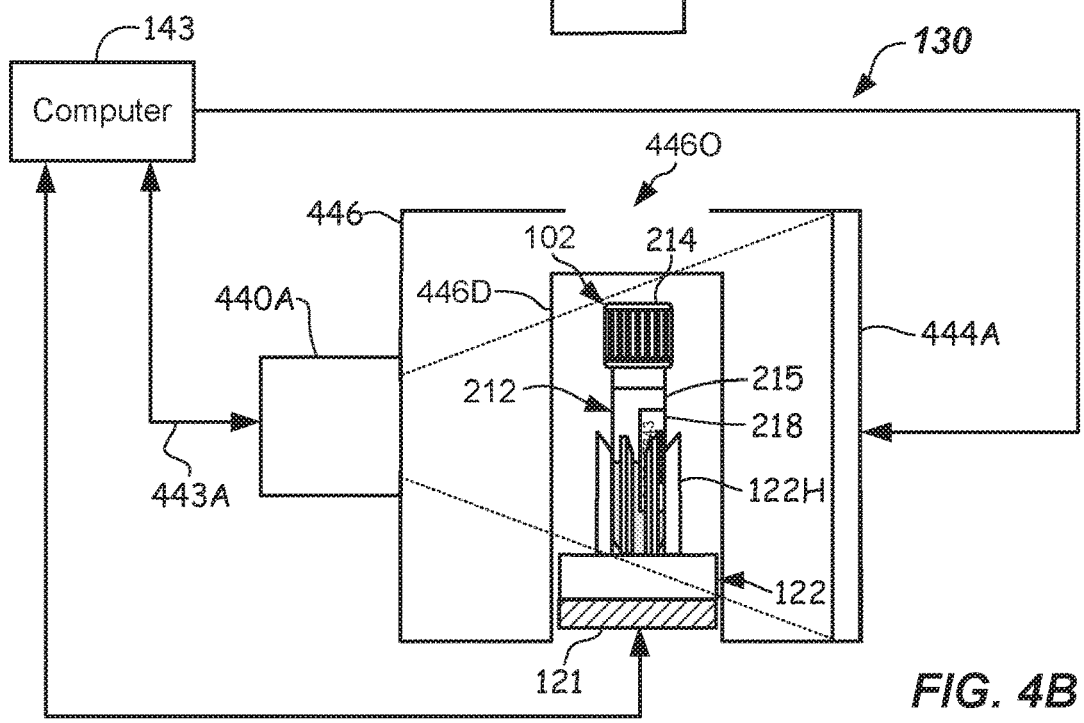
FIG. 4B illustrates a schematic side view of the quality check module (with front enclosure wall removed) of FIG. 4A according to one or more embodiments.
Figure 5:
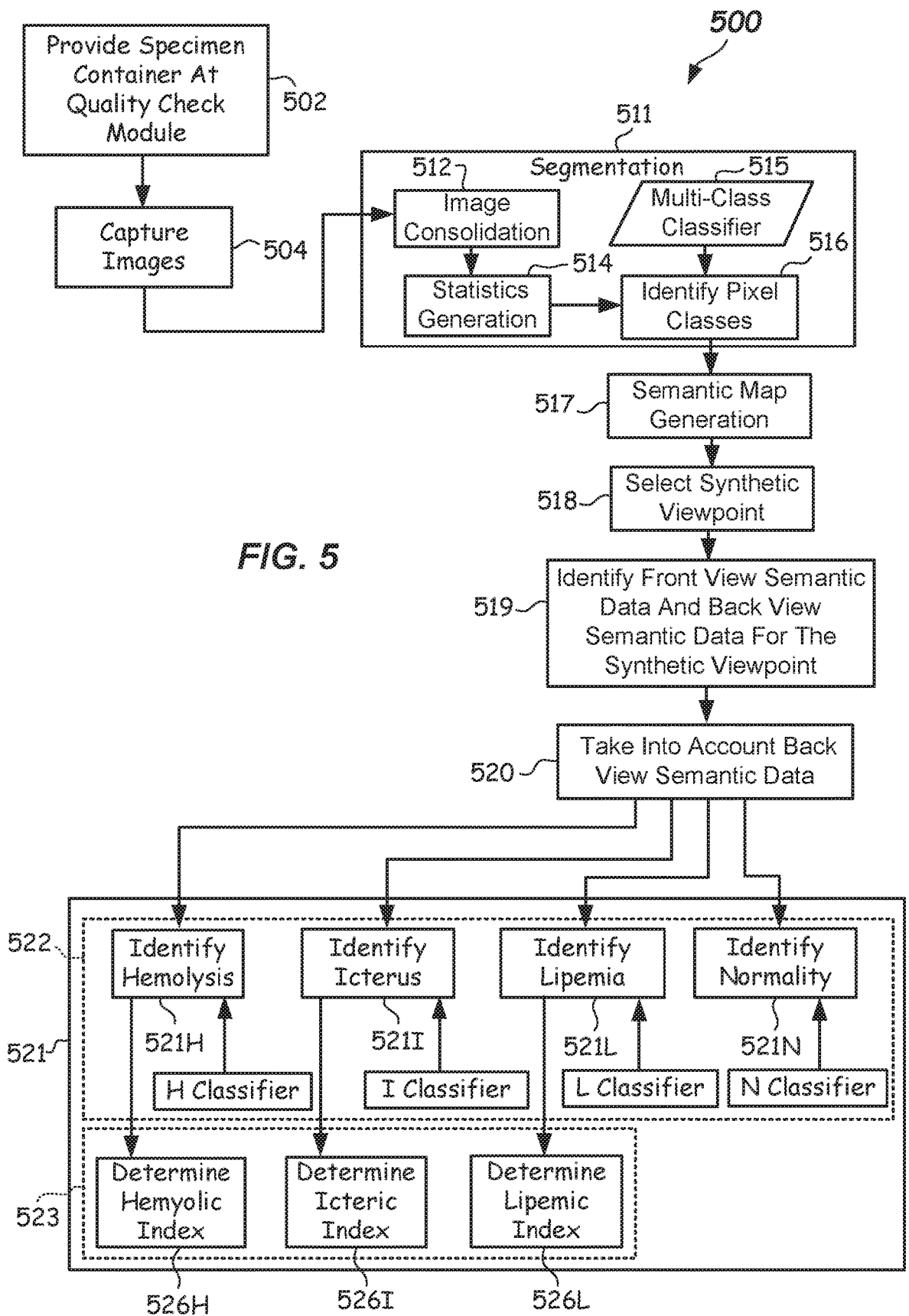
FIG. 5 illustrates a block diagram of functional components of a quality check module configured to determine a presence of H, I, and/or L or N in a specimen according to one or more embodiments.

With reference to FIGS. 4A-4B, a first embodiment of a quality check module 130 is shown and described. Quality check module 130 may be configured and adapted to automatically determine a presence of an interferent (e.g., H, I, or L) in a specimen 212 (e.g., in a serum or plasma portion 212SP thereof) prior to analysis by the one or more analyzers 106, 108, 110. Pre-screening in this manner allows for additional processing, additional quantification or characterization, discarding, or redraw of a specimen 212 without wasting valuable analyzer resources or possibly having the presence of an interferent affect the veracity of the test results.

In addition to the interferent detection method, other detection methods may take place on the specimen 212 contained in the specimen container 102 at the quality check module 130. Further, a method may be carried out at the quality check module 130 to quantify the specimen 212. For example, the quality check module 130 may be used to quantify the specimen 212, i.e., determine certain physical dimensional characteristics of the specimen 212 (e.g., a physical location of LA and SB, and/or determination of HSP, HSB, and/or HTOT, and/or a volume of the serum or plasma portion (VSP) and/or a volume of the settled blood portion (VSB)). Further, in some embodiments, an artifact detection method may determine the presence or absence of an artifact (e.g., clot, bubble, or foam).

Furthermore, the quality check module 130 may be used to quantify the specimen container 102, i.e., quantify certain physical dimensional characteristics of the specimen container 102, such as the location of TC, HT, and/or W or Wi of the specimen container 102, and/or a color of and/or type of the cap 214.

Now referring to FIGS. 1, 4A, and 4B, a first embodiment of a quality check module 130 may include multiple image capture devices 440A-440C. Three image capture devices 440A-440C are shown, but two or more, three or more, four or more can be used. Image capture devices 440A-440C may be conventional digital cameras capable of capturing a digital image (i.e., a pixelated image), charged coupled devices (CCD), an array of photodetectors, one or more CMOS sensors, or the like. For example, the three image capture devices 440A, 440B, 440C are illustrated in FIG. 4A and are configured to capture images from three different lateral viewpoints. Each image capture devices 440A, 440B, 440C may be a device capable of capturing an image having an image size. In one embodiment, the image size may be about 2560×694 pixels, for example. In another embodiment, the image size may be about 1280×387 pixels, for example. Other pixel densities may be used. Each image capture devices 440A, 440B, 440C may be configured and operable to capture lateral images of at least a portion of the specimen container 102, and at least a portion of the specimen 212. For example, the image capture devices 440A-440C may capture a part of the label 218 or cap 214 and part of the tube 215. Eventually, from the multiple images, a composite model of the specimen 212 in the specimen container 102 can be developed. The composite model may be a 3D model in some embodiments, and may be used to make final determinations about the specimen 212. In embodiments herein, the model may be a semantic model which has taken into account the presence of structures (e.g., label 218 and/or holder 122H) on the backside that may be affecting the transmitted light.

In the embodiment shown, the plurality of image capture devices 440A, 440B, 440C are arranged around the specimen 212 and configured to capture lateral images from multiple viewpoints. The viewpoints may be spaced so that they are approximately equally spaced from one another, such as about 120 degrees from one another, as shown, when three image capture devices 440A, 440B, 440C are used. As depicted, the image capture devices 440A, 440B, 440C may be arranged around the track 121. Other arrangements of the plurality of image capture devices 440A, 440B, 440C may be used. In this way, the images of the specimen 212 in the specimen container 102 may be taken while the specimen container 102 is residing in the carrier 122. The multiple images may overlap slightly.

In one or more embodiments, the carriers 122 may be stopped at the pre-determined location in the quality check module 130, such as at an imaging location, i.e., at a point where normal vectors from each of the image capture devices 440A, 440B, 440C intersect. In some embodiments, a gate may be provided to stop the carriers 122, so that one or more good quality images may be captured thereat. In other embodiments, the carriers 122 may include a linear motor configured to start and stop the carrier 122 at preset locations, as programmed. In an embodiment where there is a gate at the quality check module 130, one or more sensors (like sensors 116) may be used to determine the presence of a carrier 122 at the quality check module 130.

The image capture devices 440A, 440B, 440C may be provided in close proximity to and trained or focused to capture an image window, i.e., an area including an expected location of the specimen container 102, wherein the specimen container 102 may be stopped so that it is approximately located in a center of the view window. As configured, the image capture devices 440A, 440B, 440C can capture images that include portions of the serum or plasma portion 212SP, portions of the settled blood portion 212SB, and some, or all, of the cap 214. Within the images captured, one or more reference datum may be present. The reference datum may aid in quantification of the specimen 212. Reference datum may be TC or the bottom-most portion of the specimen container 102, or a mark placed in a known location somewhere on the specimen container 102 that van be viewed from all viewpoints, for example.

In operation, each image may be triggered and captured responsive to a triggering signal provided in communication lines 443A, 443B, 443C that may be sent by the computer 143. Each of the captured images may be processed according to one or more embodiments of the method provided herein. In one particularly effective method, HDR processing may be used to capture and process the images, although it should be understood that other imaging processing methods may be used.

In more detail, in accordance with one or more embodiments, multiple images are captured of the specimen 212 (e.g., the specimen separated by fractionation) at the quality check module 130 at multiple different exposure times and as illuminated at one or more different spectra. For example, each image capture device 440A, 440B, 440C may take 4-8 images at different exposure times at one or more spectra.

In one embodiment, the multiple spectral images may be accomplished using different colored light sources 444A-444C emitting different spectral illumination. The light sources 444A-444C may back light the specimen container 102 (as shown). A light diffuser may be used in conjunction with the light sources 444A-444C in some embodiments. The multiple different spectra light sources 444A-444C may be RGB light sources, such as LEDs emitting two or more different spectra, such as nominal wavelengths of 634 nm+/−35 nm (Red), 537 nm+/−35 nm (Green), and 455 nm+/−35 nm (Blue). In other embodiments, the light sources 444A-444C may emit one or more spectra having a nominal wavelength between about 700 nm and about 1200 nm.

For example, to capture images at a first wavelength, three red light sources (wavelength of about 634 nm+/−35 nm) may be used to illuminate the specimen 212 from three lateral locations. The red illumination by the light sources 444A-444C may occur as the multiple images (e.g., 4-8 images or more) at different exposure times are captured by each image capture device 440A-440C. In some embodiments, the exposure times may be between about 0.1 ms and 256 ms. Other exposure times may be used. Each of the respective images for each image capture device 440A-440C may be taken simultaneously.

In each embodiment, the quality check module 130 may include a housing 446 that may at least partially surround or cover the track 121, and the specimen container 102 may be located inside the housing 446 during the image taking phase. Housing 446 may include one or more doors 446D to allow the carriers 122 to enter into and/or exit from the housing 446. In some embodiments, the ceiling may include an opening 446O to allow a specimen container 102 to be loaded into the carrier 122 by a robot including moveable robot fingers from above.

Once the red illuminated images are captured in the embodiment of FIGS. 4A-4B, the red spectral light sources 444A-444C may be turned off and another spectra of light, for example, green spectral light sources 444A-444C may be turned on (nominal wavelength of about 537 nm with a bandwidth of about +/−35 nm), and multiple images (e.g., 4-8 or more images) at different exposure times may be captured at that spectra by each image capture device 440A, 440B, 440C. This may be repeated with blue spectral light sources 444A-444C (nominal wavelength of about 455 nm with a bandwidth of about +/−35 nm) for each image capture devices 440A, 440B, 440C. The different nominal wavelength spectral light sources 444A-444C may be accomplished by light panels including banks of different colored light sources that can be selectively turned on and off, for example. Other means for backlighting may be used. Further, additional spectral sources may be used for illumination in addition to or as an alternative to the RGB sources, such as infrared (IR), and/or near infrared (near IR).

The multiple images taken at multiple exposure times for each respective wavelength spectra may be obtained in rapid succession, such that the entire collection of images for the specimen 212 from multiple viewpoints may be obtained in less than a few seconds, for example. In one example, 4 different exposure images for each wavelength at three viewpoints using the image capture devices 440A, 440B, 440C and back lighting with RGB light sources 444A-444C will result in 4 images×3 colors×3 cameras=36 images. In some embodiments, multiple images are captured using white light and then RGB images may then captured by separating the white light images taken into the individual RGB components thereof. Thus, after separation, 36 images may also be captured using this methodology. The image data may be stored in memory of the computer 143 and subsequently processed thereby. Reference images may be taken in addition to the images.

According to one or more HIL characterization methods, the processing of the image data may involve, for example, selection of optimally-exposed pixels from the multiple captured images at the different exposure times at each wavelength spectra and for each image capture device 440A-440C, so as to generate optimally-exposed image data for each spectrum and for each viewpoint. This is referred to as "image consolidation" herein. For each corresponding pixel (or superpixel/image patch), for each of the images from each image capture device 440A-440C, pixels (or superpixels/image patches) exhibiting optimal image intensity may be selected from each of the different exposure time images for each viewpoint. In one embodiment, optimal image intensity may be pixels (or superpixels/image patches) that fall within a predetermined range of intensities (e.g., between 180-254 on a scale of 0-255), for example. In another embodiment, optimal image intensity may be between 16-254 on a scale of 0-255), for example. If more than one pixel (or superpixel/image patch) in the corresponding locations of two images is determined to be optimally exposed, the higher of the two is selected. The selected pixels (or superpixels/image patches) exhibiting optimal image intensity may be normalized by their respective exposure times. The result is a plurality of normalized and consolidated spectral image data sets for the illumination spectra (e.g., R, G, B, white light, IR, and/or IR) for each image capture device 440A-440C where all of the pixels (or superpixels/image patches) are optimally exposed (e.g., one image data set per spectrum.

As part of a calibration process of the quality check module 130, reference images without a specimen container 102 or carrier 122 may be taken. In this way, computational burden may be minimized by subtracting tube background (the region outside of the specimen container 102) from each image data set. Reference images for each exposure time and lighting condition (e.g., R, G, B, white light, IR, and/or near IR) may be taken by the quality check module 130 before carrying out the interferent detection method.

For each image data set including optimally-exposed pixels (or superpixels/image patches), a characterization process is undertaken to identify the pixels (or superpixels/image patches) that are classified as serum or plasma portion 212SP of the specimen 212. Identifying the serum or plasma portion 212SP may be based on classifying each the pixels (or superpixels/image patches) in the optimally-exposed image data. Classification may be based upon operation of a multi-class classifier generated from multiple training sets. The multi-class classifier may comprise a support vector machine (SVM) or a random decision tree, for example. Other means for determining the extent of the serum or plasma portion 212SP may be used.

To carry out the classification, first statistical data, as described above, may be computed for each of the optimally-exposed pixels (or superpixels/image patches) at the different spectra (e.g., R, G, B, white light, IR, and/or near IR) for each image capture device 440A-440C. The statistical data may include mean values and covariance up to $2^{nd}$ order, for example. The calculated statistical attributes encode specific properties of object classes and are thus used for discrimination between the different object classes by assigning class labels. Once generated, the statistical data is presented to, and operated on, by a multi-class classifier 515, which may classify the pixels (or superpixels/image patches) in the image as belonging to one of a plurality of class labels, such as 1—serum or plasma portion, 2—settled blood portion, 3—tube, 4—air, 4—cap, 6—label, 7—holder, and 8—gel separator (if used). From this, the pixels (or superpixels) making up the liquid region (i.e., the serum and plasma portion 212SP) may be identified.

The multi-class classifier 515 may be any suitable type of supervised classification model that is linear or non-linear. For example, the multi-class classifier 515 may be a support vector machine (SVM) that is either linear or kernel-based. Optionally, the multi-class classifier 515 may be a boosting classifier such as an adaptive boosting classifier (e.g., AdaBoost, LogitBoost, or the like), any artificial neural network, a tree-based classifier (e.g., decision tree, random decision forests), and logistic regression as a classifier, or the like. A SVM may be particularly effective for classification between liquids and non-liquids, such as found in the analysis of the specimen 212. A SVM is a supervised learning model with associated learning algorithms that analyzes data and recognizes patterns. SVMs are used for classification and regression analysis.

Multiple sets of training examples are used to train the multi-class classifier 515, and then the image data set is operated on multi-class classifier 515 and each pixel (or superpixel) is classified. The multi-class classifier 515 may be trained by graphically outlining various regions in a multitude of examples of specimen containers 102 having various specimen conditions, occlusion by label 218, occlusion by holder 122H, levels of serum or plasma portion 212SP and settled blood portions 212SB, and the like. As many as 500 or more images may be used for training the multi-class classifier 515. Each training image may be outlined manually to identify and teach the multi-class classifier 515 the areas that belong to each class.

A training algorithm builds the multi-class classifier 515 that assigns pixels (or superpixels/image patches) of any new specimens that are imaged into one of the classes. The SVM model represents examples as points in space that are mapped so that the examples of the separate classes are divided by a clear gap that is as wide as possible. New pixels from the image data set may be mapped into that same space and predicted to belong to a particular class based on which side of the gap they fall on. In some embodiments, SVMs can efficiently perform a non-linear classification using what is called a kernel trick (e.g., kernel-based SVM classifier), implicitly mapping their inputs into high-dimensional feature spaces. SVM and boosting are particularly preferred. Other types of classification models may be used.

From the pixel (or superpixel/image patch) identification of classes in 516, a semantic map may be generated in 517. The semantic map may be a 3D map that may be stored in a database in the computer 143, and may consolidate all the classifications (1—serum or plasma portion, 2—settled blood portion, 3—tube, 4—air, 4—cap, 5—label, 6—holder, and 7—gel separator (if used)) as a function of position (e.g., radial and axial position of the specimen container 102). The semantic map may be graphically displayed in some embodiments.

From the semantic map, a synthetic viewpoint may be chosen in 518. The synthetic viewpoint may be one of the viewpoints from which the images were captured with the image capture devices 440A-440C. In another embodiment, the synthetic viewpoint may be another viewpoint that is in between any two of the multiple lateral viewpoints from which the images were captured with the image capture devices 440A-440C. The synthetic viewpoint is a viewpoint that includes the maximum number of pixels (or superpixels/image patches) that have been classified as serum or plasma portion 212SP. In the case where synthetic viewpoint is one of the viewpoints from which the images were captured with the image capture devices 440A-440C, the selected synthetic viewpoint is chosen to be the viewpoint that exhibits the maximum number of pixels (or superpixels/image patches) that are classified at serum or plasma portion 212SP.

In some cases, two adjacent viewpoints may each include some pixels (or superpixels/image patches) identified at serum or plasma portion 212SP. In this case, the synthetic viewpoint is between the two viewpoints including the image capture devices 440A-440C and the segmentation data for each viewpoint is consolidated to construct a synthetic viewpoint including the regions classified at serum or plasma portion 212SP from each respective viewpoint. In this embodiment, the respective area reflecting serum or plasma portion 212SP in the synthetic viewpoint may be enlarged as compared to either of the individual viewpoints. Thus, better characterization of HILN may be carried out because of the larger amount of classified pixels (or superpixels/image patches), as will be apparent from the following.

Once the synthetic viewpoint has been selected in 518, front view data and back view data for the synthetic viewpoint may be identified in 519. The back view data is the classification and corresponding position data for the backside. The back view data may be data on the pixels (or superpixels/image patches) that have been classified during the segmentation in 511 as being either label 218, or holder 122H.

Because the backlight from the light sources 444A-444C onto the backside of the specimen container 102 in each viewpoint may be blocked by the presence of the label 218 and/or holder 122H that are located on the backside, the intensities of the front view image captured by the image capture devices 440A-440C in front view regions corresponding to the back view regions containing the label 218 and/or holder 122H may be affected. As such, the intensities in those regions may be suspect (e.g., artificially low) and therefore should not be used as-is for the HILN detection. Therefore, according to one or more embodiments of the disclosure, the method takes into account the back view data in 520.

Figure 6A:
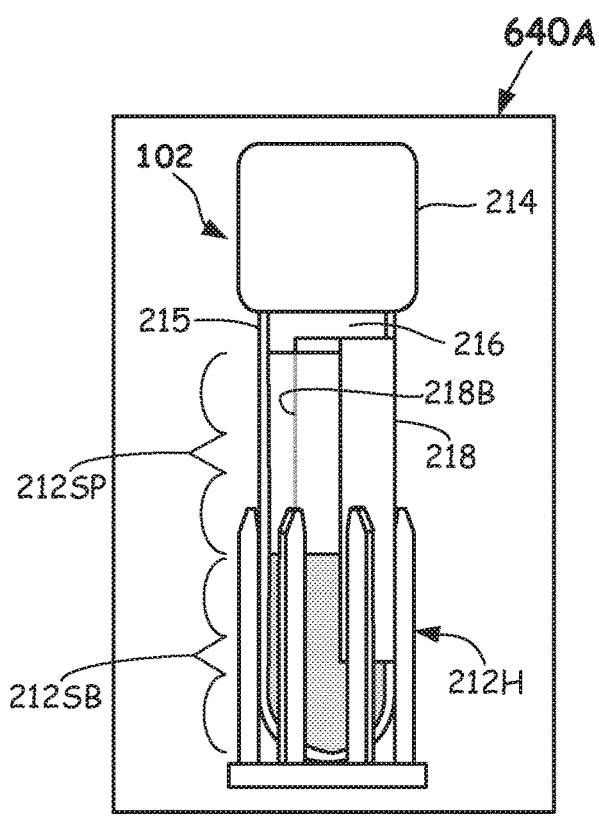
FIG. 6A illustrates a first segmented image from a first viewpoint of semantic map according to one or more embodiments.

In one embodiment, the taking into account the back view data in 520 may include not using corresponding regions in the front view semantic data on regions that are classified as being label 218 or holder 212H in the back view semantic data before determining HILN by the HILN classifier 521. For example, FIG. 6A illustrates a front semantic image 640A from a first viewpoint 1 of image capture device 440A (FIG. 6D). As can be seen, some of the serum and plasma is shown in FIG. 6A, some is occluded by label 218, and some of the backlight emitted from light source 444A (FIG. 4A) is blocked by the back view label portion 218B (i.e., the portion of the label 218 that is located on the backside view of the specimen container 102 in FIG. 6A).

Figure 6B:
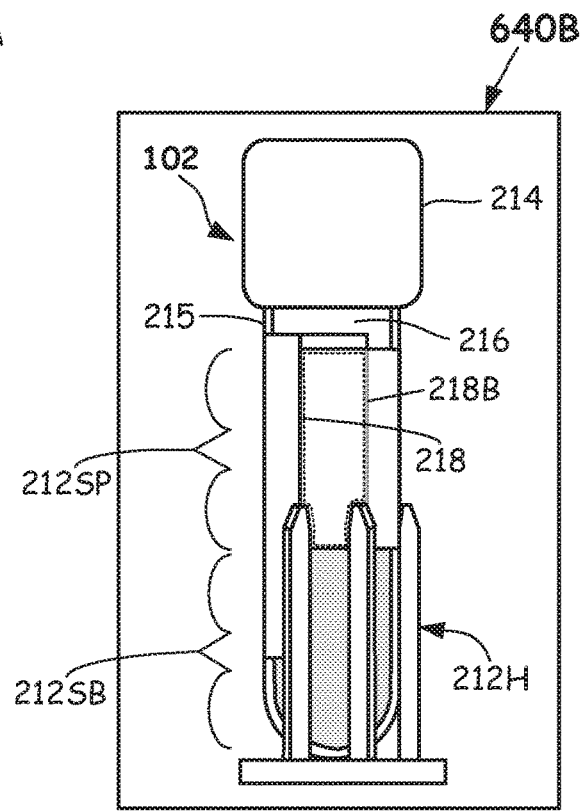
FIG. 6B illustrates a second segmented image from a second viewpoint from of a semantic map according to one or more embodiments.
Figure 6C:
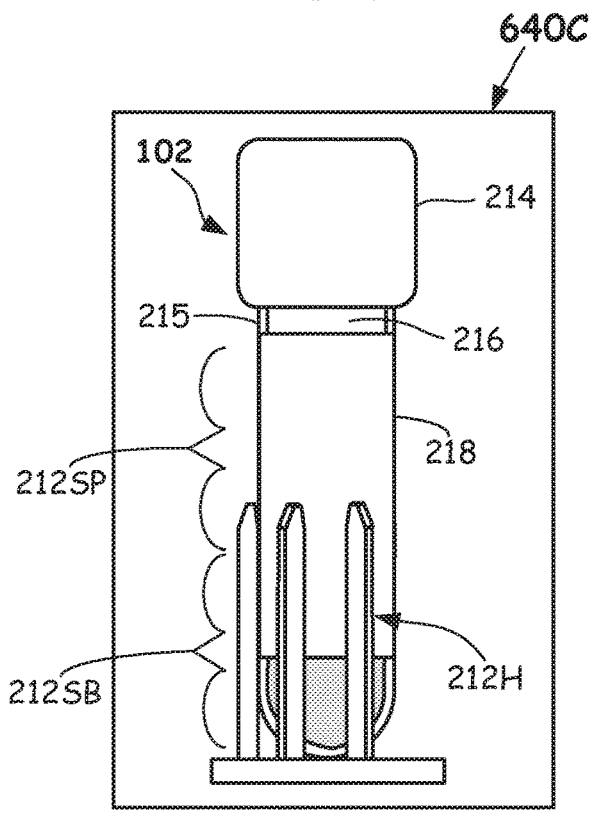
FIG. 6C illustrates a third segmented image from a third viewpoint from of a semantic map according to one or more embodiments.
Figure 6D:
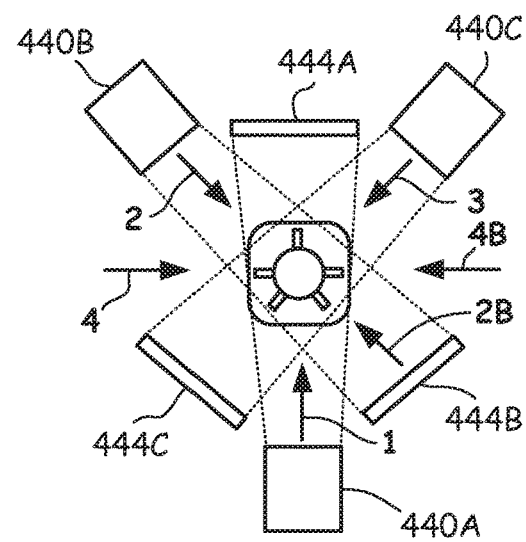
FIG. 6D illustrates a schematic top view illustrating various viewpoints according to one or more embodiments.

FIG. 6B illustrates a front semantic image 640B from a second viewpoint 2 of image capture device 440B (FIG. 6D). In FIG. 6B, some of the serum or plasma portion 212SP is occluded by label 218, and some of the backlight emitted from light source 444B (FIG. 6D) is blocked by the back view label portion 218B (i.e., the portion of the label 218 that is located on the backside of the specimen container 102 in FIG. 6B).

Figure 6E:
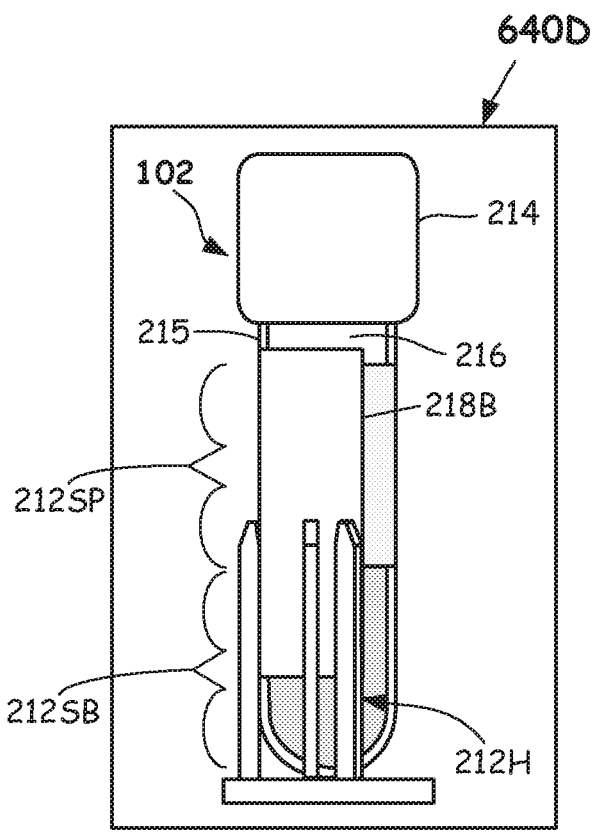
FIG. 6E illustrates a semantic back view from a synthetic viewpoint according to one or more embodiments.

FIG. 6C illustrates a front semantic image 640C from a third viewpoint 3 of image capture device 440C (FIG. 6D). In FIG. 6C, all of the serum or plasma portion 212SP is occluded by label 218. Thus, if the method chooses the synthetic viewpoint in 518 to be one of these three viewpoints (1, 2, or 3), then the second viewpoint 2 of FIG. 6D would be chosen. This is because it is the viewpoint, as illustrated in FIG. 6B, that has the most pixels (or superpixels/image patches) that have been classified as serum or plasma portion 212SP, such as determined from the semantic map generated in 518. In this case, the corresponding region in the front semantic image 640B of the serum or plasma portion 212SP that has been blocked by the label (the region shown as dotted), may be ignored and would not be used in the HILN classifier 521. This blocked portion is determined by constructing a back view semantic map or image based on the semantic map 517, which may include intensity data, classification data, and positional data collected and consolidated from all three views (1, 2, and 3). In other words, the back view data is taken into account, i.e., the knowledge of the location of the label 118 and unobstructed holder 122H is known and used to modify the corresponding regions of the second semantic front view 2. A hypothetical back view semantic map 640D is shown in FIG. 6E. This represents back view data from a back view 2B (FIG. 6D) that is taken into account in front view semantic image from viewpoint 2 (FIG. 6D). In practice, there may be no semantic back view map (like FIG. 6E), just back view semantic data that is used in the HILN classifier 521.

Figure 6F:
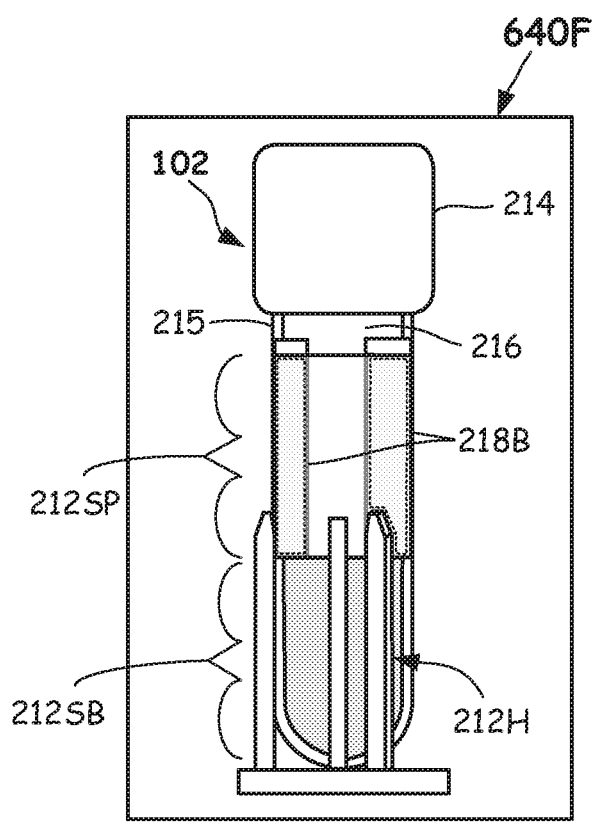
FIG. 6F illustrates a semantic front view from a synthetic viewpoint according to one or more embodiments.

In the case where the synthetic viewpoint selected in 518 is other than one of the multiple viewpoints (1-3), then a viewpoint that is a compilation of two of the other viewpoints may be selected. For example, given viewpoint 3 in FIG. 6C has the serum or plasma portion 212SP totally occluded by label 218, a viewpoint may be selected that is between viewpoint 1 and 2. This synthetic viewpoint 4 shown in FIG. 6F is a synthetic front view. This is a compilation of viewpoint 1 and viewpoint 2 and thus has approximately twice the number of pixels that are classified as serum or plasma portion 212SP. As before, in some embodiments, the data associated with the corresponding back view label portions 218B (shown as dotted in FIG. 6F) from the synthetic back view 4B can be excised from the corresponding regions in the synthetic front view data that are classified as serum or plasma portion 212SP, and not used in the HILN classifier 521. A representative front view semantic image 640F that illustrates the region classified as serum or plasma portion 212SP is shown in FIG. 6F. The data corresponding to the remaining region classified as serum or plasma portion 212SP (between the two dotted regions) is fed into the HILN classifier 521.

In other embodiments, the classifying takes into account the structures that may be present on the backside of the specimen container 102 from any selected viewpoint by modifying input to the HILN classifier 521. The "taking into account the back view semantic data" may include providing additional feature descriptors to the HILN classifier. For example, the providing additional feature descriptors may include encoding as a numerical value (e.g., a scalar value) a local feature descriptor in the representation that is presented to the HILN classifier. For example, the additional feature descriptors may be encoded as 1=label or 0=no label. Moreover, additional feature descriptors may be encoded as 1=holder or 0=no holder.

A synthetic front view semantic data, that has taken into account the back view semantic of the class serum or plasma portion 212SP may then fed into a classifier 522 configured to identify whether H, I, or L is present within the liquid region or whether no HIL is present and the serum or plasma portion 212SP is thus normal (N). Thus, effectively, the interferent classifier (e.g., HILN classifier 522), classifies based on the semantic data, whether an interferent is present within the serum or plasma portion 212SP, or is absent within the serum or plasma portion 212SP. In one or more embodiments, the interferent classifier 522 may be embodied as one or more different interferent type classifiers, such as a hemolysis classifier adapted to identify hemolysis in 521H, an icterus classifier adapted to identify icterus in 521I, a lipemia classifier adapted to identify lipemia in 521L, and a classifier adapted to identify normality in 521N. Each interferent classifier may be a binary classification model. The result of operating on the semantic data is the presence of an interferent or the absence of an interferent in the serum or plasma portion 212SP.

Hemolysis Detection

According to first broad aspect, embodiments of the disclosure are directed at a method and apparatus that may be used to detect if the specimen 212 contained in a specimen container 102 of centrifuged blood is hemolyzed. The method utilizes multiple image capture devices 440A-440C at multiple viewpoints, and may utilize multiple exposures (e.g., 4-8 exposures or more) and multiple spectral illumination (e.g., R, G, B, white light, IR, or near IR) to capture multiple pixelated spectral images. Images associated with the viewpoints are then analyzed and operated on to provide segmentation and identify the serum or plasma portion 212SP as discussed above. From this segmentation data, a semantic map may be generated. One synthetic viewpoint may be selected and front and back view semantic data may be generated therefor. This semantic data is further operated on by a HILN classifier 522 to identify hemolysis in 521H, based upon the classifier model being previously trained with a multitude of hemolyzed specimens of different hemolytic indices.

The extent or degree of hemolysis may be characterized by a hemolytic index as determined in 526H. "Hemolytic index" as used herein means a grade given to a particular specimen 212 based upon the determined content of hemolysis present in the serum or plasma portion 212SP. The grading scale for observation ranges may range from zero through four (0-4). Zero represents substantially no hemolysis while four represents significant hemolysis. Alternately, a scale of 0-10, 0-20, A-F, or some other range could be used. A specimen 212 having a sufficiently high hemolytic index, as determined by the quality check module 130, may be rejected. A usual procedure is to redraw another specimen 212 from the patient to ensure that a specimen 212 of good quality presented to the analyzer 106, 108, and/or 110. Thus, the specimen 212 exhibiting hemolysis may be rejected and offloaded at loading area 105 without being further tested. Optionally, the specimen 212 may be tested in another quality check module, and depending on the test ordered, the hemolysis index may be reported along with the test results.

Once a specimen 212 is processed, and is deemed to be normal (N) by quality check module 130 and normality classifier at 521N, it may be successfully analyzed without the interfering hemoglobin. If the specimen 212 is found to contain a sufficient level of hemolysis in 521H, an alert may be displayed on a display (e.g., computer screen) of the computer 143 or CIM 145 of the specimen testing apparatus 100 to alert lab personnel so that they may order further evaluation and/or make further decisions when the specimen 212 is found to contain hemolysis.

To improve an ability to convey the assessment of a specimen 212 containing hemolysis to laboratory personnel, an image of the specimen container 102 including the specimen 212 having hemolysis may be displayed on a display of the computer 143 or of the CIM 145. This image may be displayed along with other collaborative information such as, but not limited to, reference images of various known hemolyzed specimens, color spectra for comparison, the assessed index level of hemolysis of the specimen 212, and/or suggested laboratory personnel action to take.

Icterus Detection

According to another broad aspect, embodiments of the disclosure are directed at a method and apparatus that may be used to detect icterus in a serum or plasma portion 212SP contained in a specimen container 102 of centrifuged blood. An icterus interferent may arise, for example, from an excess of bilirubin, the result of decaying red blood cells being converted into bilirubin in the spleen. Levels of bilirubin above 2-3 mg/dl are visibly dark yellowish or brownish in color and may adversely affect any enzyme-based immunoassays carried out on the analyzers (e.g., analyzers 106, 108, and/or 110). Such a condition is also termed bilirubinaemia.

The icterus detection method is similar to that for detecting hemolysis. After image capture and performing an analysis of the pixelated images provide segmentation in 511, the semantic data, which has had the back view semantic data accounted for (accounting for presence of light blocking label 218 and/or holder 122H), may be analyzed for the presence of icterus. According to the method, the same semantic data that was operated on for the hemolysis detection may be used for icterus detection. The analysis may use a properly-trained binary classifier to determine is icterus is present, and if so, may determine an interferent level, such as an icteric index. "Icteric index" as used herein means the grade given to a particular specimen 212 based upon the determined content of icterus present. The grading scale for observation may range from zero through four (0-4). Similarly, zero represents substantially no icterus, while four represents significant presence of icterus. Alternately, scales could be used, such as 0-10, 0-20, A-F, or some other range.

Lipemia Detection

According to another broad aspect, embodiments of the disclosure are directed at a method and apparatus that may be used to detect lipemia in a specimen 212 contained in a specimen container 102 of centrifuged blood. A lipemia interferent, which may exhibit a whitish appearance in the serum or plasma portion, may arise from the presence of excess lipids in the blood. Lipid levels above about 50 mg/dl may interfere with antibody binding in immunoassay testing and may therefore affect an immunoassay result from the analyzer 106, 108, or 110.

The lipemia detection method is similar to that for detecting hemolysis and icterus. The method may receive the specimen container 102 at the quality check module 130. Next, image capture devices 440A-440C may capture pixelated images of the specimen 212 from multiple viewpoints. The computer 143 may then perform an analysis of the images to segment the specimen container 102 and specimen 212 in 511. From the segmentation, the semantic map may be generated in 517. Finally, the semantic data may be operated on to determine the presence of lipemia in HILN classifier 521. According to the method, the same semantic data that was used for the hemolysis and icterus detection may be operated on to determine the presence of lipemia. The analysis may determine if a lipemia interferent is present by using a trainer L classifier model to identify lipemia in 521L, and if so, an interferent level, such as a lipemic index. A trained lipemia classifier may be used to determine lipemia in 521L. Any suitable classifier may be used, such as a SVM. "Lipemic index" as used herein means the grade given to a serum or plasma portion 212SP based upon the determined content of lipemia therein. The grading scale for visual observation may range from zero through four (0-4). Similarly, zero represents substantially no lipemia, while four represents significant presence of lipemia. Alternately, other scales could be used, such as 0-10, 0-20, A-F, or some other range. Lipemia is a specific sample quality discoloration defect, which may be resolved with special processing before the specimen 212 is tested or analyzed on an analyzer (e.g., analyzer 106, 108, 110). Other grading scales may be used.

After the lab is aware the specimen is lipemic, they may further process the specimen 212 at another location (e.g., at station 132) to remove or reduce the lipids. For example, they may introduce a solvent or other material to reduce the amount of lipemia. Following the additional processing to lower the lipemia level at station 132, the specimen 212 can be returned to the track 121 and may be placed directly on an analyzer (e.g., analyzer 106, 108, 110) for analysis. Optionally, the specimen 212 may again be routed to the quality check module 130 so to rescreen the specimen for lipemia in accordance with the method disclosed herein. If the lipemia level is now sufficiently low, then the specimen may be routed on track 121 to be analyzed on the analyzer (e.g., analyzer 106, 108, or 110), wherein thereafter the specimen 212 may be returned to the loading area 105.

Normality Detection

The specimen 212 may also be analyzed for normality (N), i.e., the lack of H, I, and L. The normality detection method may receive the specimen container 102 at the quality check module 130. The method may receive the specimen container 102 at the quality check module 130. Next, image capture devices 440A-440C may capture pixelated images of the specimen 212 from multiple viewpoints. The computer 143 may then perform an analysis of the images to segment the specimen container 102 and specimen 212 in 511. From the segmentation, the semantic map may be generated in 517. Finally, the image data may be analyzed for the presence of normality in HILN classifier 521. According to the method, the same semantic data that was used for the previously-described hemolysis, icterus, and lipemia detection may be operated on to determine normality. A trained normality classifier may be used to determine normality in 521N. Any suitable classifier may be used, such as a SVM.

Thus, it should be apparent that embodiments of the disclosure may detect H, I, and/or L, or N at the first possible instance (e.g., at the quality check module 130) after centrifugation of the specimen 212. By detecting H, I, and/or L or N at this point in the process, the specimen 212 will not be wasted, erroneous test results may be prevented, and any patient test result delay will be minimized. In some embodiments, to provide an even more accurate measurement of the level of H, I, and/or L present in the serum or plasma portion 212SP, an artifact detection method may be employed to identify a presence of an artifact, such as clot, bubble, or foam. The pixels identified as containing one or more artifacts in the serum or plasma portion may be ignored in the front view semantic data for the synthetic viewpoint and not used in the HILN classifier 521. The artifact detection method of 622 (FIG. 6) is further described in co-pending U.S. Provisional Patent Application 62/288,358 filed Jan. 28, 2016, and entitled "Methods And Apparatus For Classifying An Artifact In A Specimen."

According to the method, the identifying hemolysis in 521H, identifying icterus in 521I, identifying lipemia in 521L, and identifying normality in 521N may be carried out by operating of the semantic data with a HILN classifier 521 that is trained based on multiple training sets. In one embodiment, individual binary classifiers may be used for each of H, I, L, and N. Optionally, a multi-class classifier may be used for identifying any one or more of H, I, L, or N. The multi-class classifier (e.g., a four class classification model) may be a support vector machine (SVM), support-vector network, or a boosting class algorithm. Examples of support vector machines and networks are described in a paper entitled "Support-vector Networks" by C. Cortes and V. Vapnik in Machine Learning Vol. 20, Issue 3, page 273-297, in a paper entitled "Additive Logistic Regression: A Statistical View of Boosting" by J. Friedman, T. Hastie, R. Tibshirani (1998), and "A Short Introduction to Boosting" by Y. Freund and R. E. Schapire (1999). Optionally, the R, G, B, and/or white light illuminated intensity values for each pixel (or superpixel/image patch) of the semantic data can be compared against R, G, B, and/or white light value ranges stored in memory, such as in a lookup table to determine H, I, L, or N.

In one or more embodiments, the determination of the presence of one or more interferent involves first analyzing the semantic data on a pixel (or superpixel/image patch) basis, taking into account the back view data of the synthetic viewpoint, to characterize individual ones of the pixels (or superpixels/image patches) as being either normal (N), or containing Hemolysis (H), Icterus (I) or Lipemia (L). From this determination, an overall classification of the serum or plasma portion 212SP may be provided. The overall classification may be as being normal (N) or including a particular type or types of interferent. For example, the particular interferent type(s) may be determined to be one of H, I, and/or L, such as H, I, or L, H and I, H and L, I and L, or H, I, and L.

The determination that the serum or plasma portion 212SP is, as a whole, H, I, and/or L, or N may be accomplished by adding a number of pixels (or superpixels/image patches) in the serum or plasma portion 212SP that have been classified by the HILN classifier 521 as being N, H, I, or L. The classification as normal (N) or as containing an interferent may be based upon a largest number of pixels (or superpixels/image patches) in each class, or a weighting scheme in some embodiments. Thus, in one embodiment, if a majority of pixels (or superpixels) are classified as N, then the serum or plasma portion 212SP may be categorized as normal (N). If a majority of pixels (or superpixels/image patches) are classified as H, then the serum or plasma portion 212SP may be categorized as containing hemolysis (H). Likewise, if a majority of pixels (or superpixels/image patches) are classified as I or L, then the serum or plasma portion 212SP may be categorized as Icterus (I), or lipemia (L), respectively. In other embodiments, a weighted majority voting scheme may be also used to classify the specimen 212 using probabilities from the HILN classifier 521 as a weight. Other means for characterizing the serum or plasma portion 212SP, as a whole, may be used.

Moreover, if the semantic data set contains a relatively large amount of pixels (or superpixels/image patches) that are classified in two or more interferent classes (e.g., H and I, H and L, I and L, or even H, I, and L), then the interferent detection method may report that multiple interferent types are present. Once the specimen 212 has been given a characterization as containing multiple interferent types (e.g., H, I, and/or L), the interferent level detector 523 may be used to provide an interferent level for the multiple interferent types in the serum or plasma portion 212SP. Interferent level detector 523 may obtain an interferent level or index for each particular interferent by passing the semantic data set through a level characterizing model, such as a supervised regression model. Any suitable regression model may be used, such as support vector regression (SVR), neural network regression, tree-based regression, or the like.

A different regression model may be used for each interferent type, such as hemolysis regression model 526H, icterus regression model 526I, and lipemia regression model 526L. In one or more embodiments, each of the regression models may be an SVR machine and may be trained using a liquid region that exhibits that particular type of interferent type (e.g., H, I, or L). For example, the hemolysis regression model 526H may be trained with a broad range of specimens 212 having hemolysis levels across a diverse range of expected hemolysis levels. For example, hemolysis ranges may include hemolysis levels from about 50-525. Likewise, the icterus regression model 526I may be trained with a broad range of specimens 212 having icterus levels across a diverse range of expected levels, including icterus levels from about 1.7 to 30. Similarly, lipemia regression model 526L may be trained with a broad range of specimens 212 having lipemia levels across a diverse range of expected levels, including lipemia levels from about 125-1,000.

In some embodiments, the interferent levels may be discretized. For example, four discreet levels may be used. For the hemolysis regression model 526H, discreet hemolysis levels of 50, 150, 250, and 525 may be used. For the icterus regression model 526I, discreet icterus levels of 1.7, 6.6, 16, and 30 may be used, and for the lipemia regression model 526L, discreet lipemia levels of 125, 250, 500, and 1,000 may be used. More or less than four discreet levels may be used.

Although the results from the multiple viewpoints may offer an indication of whether the specimen is normal (N) or contains on more of HIL, the final determination of the interferent level may be determined by fusing of the regression results of the data sets of that particular interference type as passed through the regression models. If the interference levels of the model have been discretized, then the output from the regression models will also be discretized by mapping to the closest target level. In any event, according to one or more embodiments, an interferent level or index may be provided for each detected interferent type.

Accordingly, it should be apparent that the interferent detection and classification method carried out by the quality check module 130 may result in a rapid characterization of the specimen 212 as being either normal N or containing one or more interferent HIL therein. If the specimen 212 contains one or more interferent, then the method may further determine the interferent type or types present, and may also determine an interferent level or index for each interferent type present.

Figure 7:
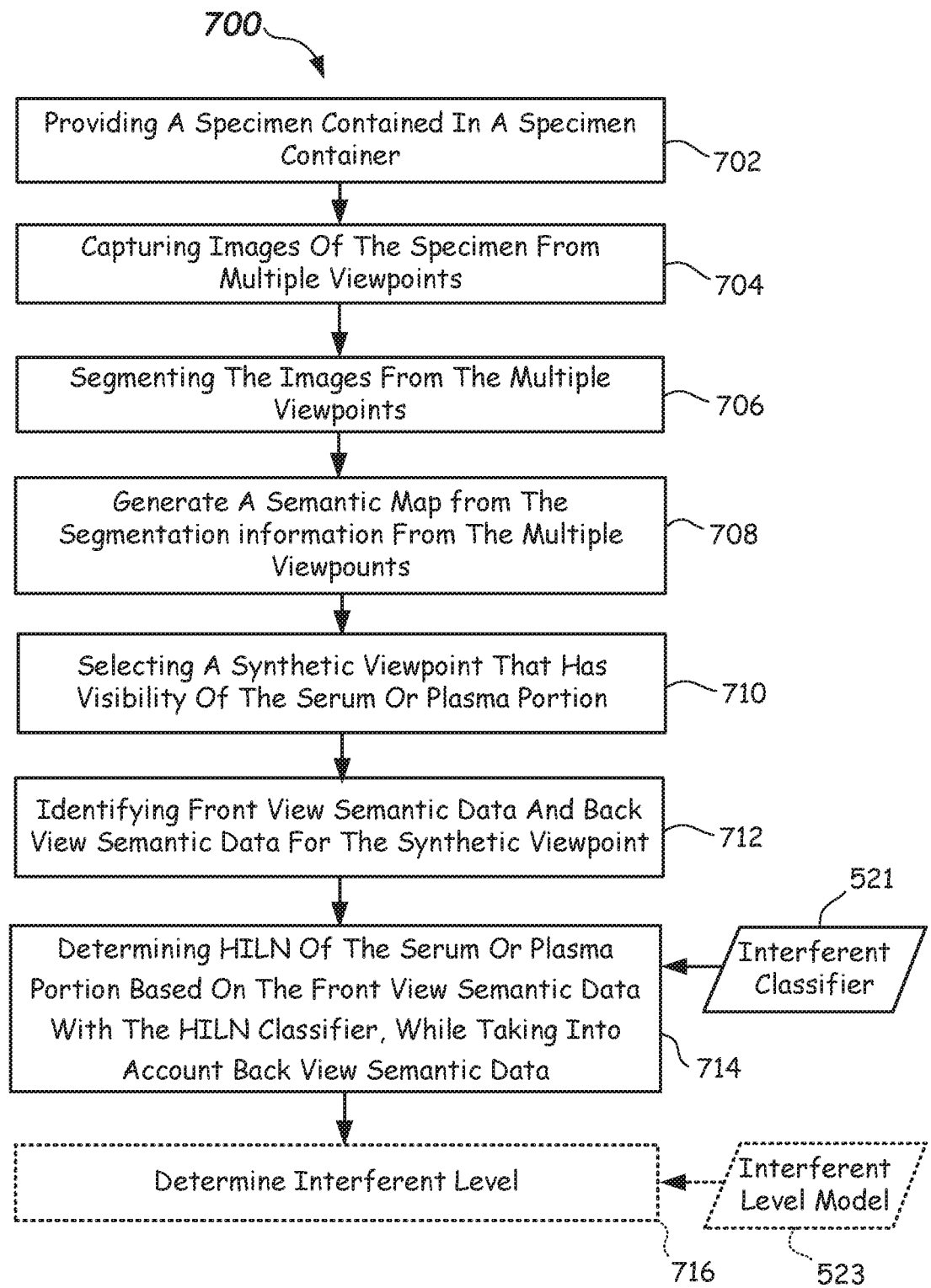
FIG. 7 is flowchart of a method of determining H, I, and/or L, or N in a specimen according to one or more embodiments.

FIG. 7 illustrates a flowchart of a method of determining an interferent in a specimen 212 according to one or more embodiments. The method 700 includes providing a specimen (e.g., specimen 212) contained in a specimen container (e.g., specimen container 102, such as a capped, blood collection tube) in 702. Next, the method 700 includes capturing images of the specimen container 102 containing specimen 212 from multiple viewpoints in 704. The specimen container 102 may be held in a holder 122H and some portion of the specimen container 102 may include a label 218 provided thereon. An image capture device 440A-440C as described above may be used for image capture. The multiple images may include multiple images at each viewpoint at different exposure times and/or at different spectra (e.g., R, G, B, white light, IR, and/or near IR). For example, there may be 4-8 different exposures or more taken at different exposure times in some embodiments, but under the same lighting conditions. In one or more embodiments, some images may be captured using white light as the backlighting light source 444A-444C and some may be captured using a plurality of single-wavelength peak, narrow-band spectral light sources, such as red, blue and green as backlit light sources 444A-444C.

The method 700 may include, in 706, processing the one or more images from the multiple viewpoints to provide segmentation information for each viewpoint by determining classifications of regions for each viewpoint. The segmentation of the images from the various viewpoints may involve selecting optimally-exposed pixels (or superpixels/image patches) from the images at different exposure times at each spectrum to generate optimally-exposed image data at each spectrum and viewpoint. For each corresponding pixel (or superpixel/image patch) location in each image at a particular spectra and viewpoint, the best exposed pixel (or superpixel/image patch—not under or over exposed) is selected. The optimal exposure range may be as discussed above. This selecting optimally-exposed pixels (or superpixels/image patches) may take place in an image consolidation phase (e.g., image consolidation 512). Thus, for each of the illuminated spectra, a data set of optimally-exposed pixels (or superpixels/image patches) may be generated.

Next, the method 700 may include classifying the optimally-exposed pixels (or superpixel/image patch). Classifying may be accomplished by computing statistical data of the optimally-exposed pixels (or superpixels/image patches) at the different spectra to generate statistical data, and then operating on the statistical data to identify the various classes in the image data. Segmentation in 511 may include determining classes (e.g., serum or plasma portion 212SP, settled blood portion 212SB, air 212A, tube 212T, label 218, holder 122H, and/or gel separator 313).

Once consolidation and segmentation is completed, in 708, a generating a semantic map from the segmentation information from each of the multiple viewpoints. The semantic map may be generated by aggregating the segmentation data (classification, intensity, and location data). The semantic map may be a 3D rendering and may be stored as semantic data in a database. In other embodiments, the semantic map may simply be data stored in a database.

The method 700 further includes, in 710, selecting a synthetic viewpoint that has visibility of the serum or plasma portion 212SP. The synthetic viewpoint may be one of the three viewpoints (viewpoints 1, 2, or 3—FIG. 6D) associated with the image capture devices 440A-440C or other than those, such as viewpoint 4 (FIG. 6D). The synthetic viewpoint may be selected based on the image that has the largest number of pixels (or superpixels/image patches) that have been classified as serum or plasma portion. Once the synthetic viewpoint is selected, the method 700 may, in 712, carry out identifying front view semantic data and back view semantic data for the synthetic viewpoint. This may involve identifying the collection of pixels (or superpixels/image patches) from the semantic map that will constitute the front view and the back view of the synthetic viewpoint.

The method 700 includes, in 714, determining HILN of the serum or plasma portion 212SP based on the front view semantic data with the HILN classifier 521, while taking into account back view semantic data. This may involve operating on the front view semantic data with the HILN classifier 521 wherein the back view semantic data has been taken into account, such as by removal or nonuse of data associated with selected portions or regions of the front view semantic data that correspond to label 218 and/or holder 122H in the back view semantic data, or by encoding the input to the HILN classifier 521 to include additional feature descriptors associated with the label 218 and/or holder 122H in the back view data.

Optionally, in 716, an interferent level (e.g., H, I, and/or L index) may be detected, such as by using an interferent level model such as a regression model or the like. Accordingly, based on the foregoing it should be apparent that a model-based specimen interferent detection method 700, taking into account the light-blocking structures that may be present in the back view, as carried out by the quality check module 130, may result in a rapid and robust characterization of a presence of H, I, and/or L, or N of the specimen 212. If an interferent (e.g., H, I, and/or L) is detected, an interferent level may be assessed and reported.

While the quality check module 130 has been shown in FIG. 1 as being located such that the pre-screening is performed immediately after centrifugation, it may be advantageous to include a quality check module 130 directly on an analyzer (e.g., analyzer 106, 108, and/or 110) in some embodiments, or elsewhere along the track 121. For example, a quality check module 130 may be provided at station 132 that is not physically connected to the track 121 of the specimen testing apparatus 100. The quality check module 130 could be used to validate specimens 212 prior to analysis. Furthermore, in some embodiments, the centrifugation may be performed prior to loading the racks 104 into the loading area 105, so that in some embodiments, the quality check module 130 may be located at or near the loading area 105 and the HILN determination can be carried out as soon as the robot 124 loads a specimen container 102 into a carrier 122.

Various selected components, features, or embodiments may be described individually herein. It should be noted that such components, features, or embodiments may be used in substitution with other individually-described components, features or embodiments, or even in combination with other described components, features, or embodiments, as is practical.

While the invention is susceptible to various modifications and alternative forms, specific system and apparatus embodiments and methods thereof have been shown by way of example in the drawings and are described in detail herein. It should be understood, however, that it is not intended to limit the disclosure to the particular apparatus or methods disclosed but, to the contrary, the intention is to cover all modifications, equivalents, and alternatives falling within the scope of the appended claims.

What is claimed is:

1. A method of characterizing a specimen for HILN, comprising:
   capturing one or more images from multiple viewpoints of a specimen container including a serum or plasma portion, wherein the specimen container is held in a holder and some portion of the specimen container includes a label;
   processing the one or more images from the multiple viewpoints to provide segmentation information for each of the multiple viewpoints by determining classifications of regions for each of the multiple viewpoints;
   generating a semantic map from the segmentation information from each of the multiple viewpoints;
   selecting a synthetic viewpoint that has visibility of the serum or plasma portion;
   identifying front view semantic data and back view semantic data for the synthetic viewpoint; and
   determining HILN of the serum or plasma portion based on the front view semantic data with an HILN classifier, while taking into account the back view semantic data.

2. The method of claim 1, wherein the back view semantic data includes information on regions that are classified as being label.

3. The method of claim 1, wherein the back view semantic data includes information on regions that are classified as being holder.

4. The method of claim 1, wherein the back view semantic data includes information on regions that are classified as label and holder.

5. The method of claim 1, comprising not using corresponding regions in the front view semantic data on regions that are classified as being label in the back view semantic data.

6. The method of claim 1, wherein the taking into account the back view semantic data comprises not using regions in the front view semantic data corresponding to regions that are classified as being holder in the back view semantic data.

7. The method of claim 1, wherein the semantic map includes information on at least the serum or plasma portion and the label.

8. The method of claim 1, wherein the semantic map includes information on at least the serum or plasma portion and holder.

9. The method of claim 8, wherein the semantic map includes information on one or more of holder, separator, air, tube, and cap.

10. The method of claim 1, wherein the synthetic viewpoint comprises one of the multiple viewpoints.

11. The method of claim 1, wherein the synthetic viewpoint comprises other than one of the multiple viewpoints.

12. The method of claim 1, wherein the synthetic viewpoint comprises a viewpoint other than one of the multiple viewpoints, and the front view semantic data of the synthetic viewpoint includes a most number of pixels that are designated as serum or plasma portion.

13. The method of claim 1, wherein the capturing the one or more images from the multiple viewpoints comprises backlighting with light sources comprising one or more spectra of R, G, B, white light, IR, and near IR.

14. The method of claim 1, wherein the capturing the one or more images from the multiple viewpoints comprises exposure at different exposure times for each spectral illumination.

15. The method of claim 1, comprising illumination during the capturing the one or more images at multiple different spectra comprising red light, green light, and blue light, white light, and IR light.

16. The method of claim 1, wherein the taking into account the back view semantic data comprises providing additional feature descriptors to the HILN classifier taking into account back view data before determining the HILN.

17. The method of claim 16, wherein the additional feature descriptors are encoded as 1=label or 0=no label.

18. The method of claim 16, wherein the additional feature descriptors are encoded as 1=holder or 0=no holder.

19. A quality check module adapted to determine presence of an interferent in a specimen contained within a specimen container, comprising:
   a plurality of image capture devices arranged around the specimen container and configured to capture multiple images of the specimen from multiple viewpoints; and
   a computer coupled to the plurality of image capture devices and adapted to process image data of the multiple images, the computer configured and capable of being operated to:
   generate a semantic map,
   select a synthetic viewpoint of the semantic map,
   identify front view semantic data and back view semantic data for the synthetic viewpoint, and
   classify whether an interferent is present within a serum or plasma portion of the specimen based on the front view semantic data, while taking into account the back view semantic data.

20. A specimen testing apparatus adapted to determine presence of an interferent in a specimen contained within a specimen container, comprising:
   a track;
   a carrier moveable on the track and configured to contain the specimen container;
   a plurality of image capture devices arranged around the track and configured to capture multiple images of the specimen from multiple viewpoints; and
   a computer coupled to the plurality of image capture devices and configured to process image data from the multiple images, the computer configured and capable of being operated to:
   generate a semantic map,
   select a synthetic viewpoint of the semantic map,
   identify front view semantic data and back view semantic data for the synthetic viewpoint, and
   classify whether an interferent is present within a serum or plasma portion of the specimen based on the front view semantic data, while taking into account the back view semantic data.

* * * * *